(12) United States Patent
Rajarathnam et al.

(10) Patent No.: US 11,064,870 B2
(45) Date of Patent: Jul. 20, 2021

(54) BIOPSY CAP FOR USE WITH ENDOSCOPE

(71) Applicant: BOSTON SCIENTIFIC LIMITED, Hamilton (BM)

(72) Inventors: Boopathi Rajarathnam, Salem (IN); Nishant Randhawa, S.A.S. Nagar (IN); Charudatta Chandrakant Aradhye, Solapur (IN); Swami Upadhyay, Gurgaon (IN); Vasanthan Mani, Bangalore (IN); Harchetan Singh Aneja, Gurgaon (IN); Balaji Aswatha Narayana, Bangalore (IN); Sharath Badadamath, Karnataka (IN); Ramakanteswararao Beesetty, Gurgaon (IN)

(73) Assignee: BOSTON SCIENTIFIC LIMITED, Hamilton (BM)

( * ) Notice: Subject to any disclaimer, the term of this patent is extended or adjusted under 35 U.S.C. 154(b) by 340 days.

(21) Appl. No.: 16/100,960

(22) Filed: Aug. 10, 2018

(65) Prior Publication Data
US 2019/0046016 A1    Feb. 14, 2019

Related U.S. Application Data

(60) Provisional application No. 62/544,581, filed on Aug. 11, 2017.

(51) Int. Cl.
*A61B 1/00*    (2006.01)
*A61B 10/06*    (2006.01)
(Continued)

(52) U.S. Cl.
CPC ...... *A61B 1/00137* (2013.01); *A61B 1/00094* (2013.01); *A61B 1/00128* (2013.01);
(Continued)

(58) Field of Classification Search
None
See application file for complete search history.

(56) References Cited

U.S. PATENT DOCUMENTS

| 561,059 A | 5/1896 | Mitchell et al. |
|---|---|---|
| 1,204,053 A | 11/1916 | Moore |

(Continued)

FOREIGN PATENT DOCUMENTS

| AU | 1999027921 A1 | 2/2000 |
|---|---|---|
| AU | 2001056987 A1 | 2/2000 |

(Continued)

OTHER PUBLICATIONS

Arndorfer Inc. Information Sheet, dated on or before Mar. 6, 2000, 7 sheets.

(Continued)

*Primary Examiner* — Timothy J Neal
(74) *Attorney, Agent, or Firm* — Kacvinsky Daisak Bluni PLLC

(57) ABSTRACT

Endoscope assemblies, biopsy caps, and methods for making and using the same. An example endoscope assembly may include an endoscope having a channel formed therein and a port that provides access to the channel. A cap may be coupled to the port. The cap may include a base having a securing member for securing the cap to the port, an outer shell and a brush section disposed within the interior volume adjacent the disk shutter section, the brush section including a plurality of brushes arranged in a helical fashion.

20 Claims, 48 Drawing Sheets

(51) Int. Cl.
    *A61B 1/018*      (2006.01)
    *A61B 17/00*      (2006.01)
(52) U.S. Cl.
    CPC .......... *A61B 10/06* (2013.01); *A61B 1/00154*
              (2013.01); *A61B 1/018* (2013.01); *A61B*
                              *2017/00296* (2013.01)

(56) References Cited

U.S. PATENT DOCUMENTS

| | | |
|---|---|---|
| 1,213,001 A | 1/1917 | Phillips |
| 1,901,731 A | 3/1933 | Buerger |
| 2,623,520 A | 12/1952 | Bamford, Jr. et al. |
| 3,015,869 A | 1/1962 | Rapata |
| 3,536,281 A | 10/1970 | Meehan et al. |
| 3,602,228 A | 8/1971 | Cowley |
| 3,677,243 A | 7/1972 | Nerz |
| 4,178,920 A | 12/1979 | Cawood, Jr. et al. |
| 4,198,958 A | 4/1980 | Utsugi |
| 4,198,959 A | 4/1980 | Otani |
| 4,306,562 A | 12/1981 | Osborne |
| 4,326,516 A | 4/1982 | Schultz et al. |
| 4,345,606 A | 8/1982 | Littleford |
| 4,367,905 A | 1/1983 | Nauta |
| 4,411,654 A | 10/1983 | Boarini et al. |
| 4,412,832 A | 11/1983 | Kling et al. |
| 4,474,174 A | 10/1984 | Petruzzi |
| RE31,855 E | 3/1985 | Osborne |
| 4,509,944 A | 4/1985 | King et al. |
| 4,609,370 A | 9/1986 | Morrison |
| 4,653,477 A | 3/1987 | Akui et al. |
| 4,687,470 A | 8/1987 | Okada |
| 4,696,668 A | 9/1987 | Wilcox |
| 4,700,694 A | 10/1987 | Shishido |
| 4,715,360 A | 12/1987 | Akui et al. |
| 4,723,942 A | 2/1988 | Scott |
| 4,738,666 A | 4/1988 | Fuqua |
| 4,748,982 A | 6/1988 | Horzewsk et al. |
| 4,762,129 A | 8/1988 | Bonzel |
| 4,771,777 A | 9/1988 | Horzewski et al. |
| 4,781,677 A | 11/1988 | Wilcox |
| 4,787,884 A | 11/1988 | Goldberg |
| D301,365 S | 5/1989 | Gette |
| 4,835,824 A | 6/1989 | Durham et al. |
| 4,844,092 A | 7/1989 | Rydell et al. |
| 4,858,810 A | 8/1989 | Intlekofer et al. |
| 4,867,605 A | 9/1989 | Myers et al. |
| 4,900,184 A | 2/1990 | Cleveland |
| 4,905,667 A | 3/1990 | Foerster et al. |
| 4,909,798 A | 3/1990 | Fleischhacker et al. |
| 4,917,103 A | 4/1990 | Gambale et al. |
| 4,920,953 A | 5/1990 | McGown |
| 4,927,418 A | 5/1990 | Dake et al. |
| 4,928,669 A | 5/1990 | Sullivan |
| 4,928,693 A | 5/1990 | Goodin et al. |
| 4,932,413 A | 6/1990 | Shockey et al. |
| 4,940,062 A | 7/1990 | Hampton et al. |
| 4,946,443 A | 8/1990 | Hauser et al. |
| 4,973,329 A | 11/1990 | Park et al. |
| 4,983,168 A | 1/1991 | Moorehead |
| 4,988,356 A | 1/1991 | Crittenden et al. |
| 4,995,872 A | 2/1991 | Ferrara |
| 4,997,421 A | 3/1991 | Palsrok et al. |
| 5,026,366 A | 6/1991 | Leckrone |
| 5,034,001 A | 7/1991 | Garrison et al. |
| 5,040,548 A | 8/1991 | Yock |
| 5,061,273 A | 10/1991 | Yock |
| 5,064,414 A | 11/1991 | Revane |
| 5,098,064 A | 3/1992 | Daly et al. |
| 5,106,054 A | 4/1992 | Mollenauer et al. |
| 5,125,915 A | 6/1992 | Berry et al. |
| 5,127,393 A | 7/1992 | McFarlin et al. |
| 5,127,626 A | 7/1992 | Hilal et al. |
| 5,135,535 A | 8/1992 | Kramer |
| 5,137,288 A | 8/1992 | Starkey et al. |
| 5,137,517 A | 8/1992 | Loney et al. |
| 5,139,032 A | 8/1992 | Jahrmarkt et al. |
| 5,147,377 A | 9/1992 | Sahota |
| 5,154,725 A | 10/1992 | Leopold |
| 5,158,545 A | 10/1992 | Trudell et al. |
| 5,160,323 A | 11/1992 | Andrew |
| 5,161,534 A | 11/1992 | Berthiaume |
| 5,163,941 A | 11/1992 | Garth et al. |
| 5,167,634 A | 12/1992 | Corrigan, Jr. et al. |
| 5,167,636 A | 12/1992 | Clement |
| 5,171,222 A | 12/1992 | Euteneuer et al. |
| 5,180,367 A | 1/1993 | Kontos et al. |
| 5,191,888 A | 3/1993 | Palmer et al. |
| 5,195,978 A | 3/1993 | Schiffer |
| 5,199,948 A | 4/1993 | McPhee |
| 5,205,822 A | 4/1993 | Johnson et al. |
| 5,219,332 A | 6/1993 | Nelson et al. |
| 5,219,335 A | 6/1993 | Willard et al. |
| 5,232,445 A | 8/1993 | Bonzel |
| 5,248,306 A | 9/1993 | Clark et al. |
| 5,250,033 A | 10/1993 | Evans et al. |
| 5,263,932 A | 11/1993 | Jang |
| 5,267,958 A | 12/1993 | Buchbinder et al. |
| 5,279,562 A | 1/1994 | Sirhan et al. |
| 5,281,203 A | 1/1994 | Ressemann |
| 5,282,479 A | 2/1994 | Havran |
| 5,290,232 A | 3/1994 | Johnson et al. |
| 5,290,241 A | 3/1994 | Kraus et al. |
| 5,300,085 A | 4/1994 | Yock |
| 5,304,143 A | 4/1994 | Green et al. |
| 5,306,247 A | 4/1994 | Pfenninger |
| 5,308,318 A | 5/1994 | Plassche, Jr. |
| 5,314,408 A | 5/1994 | Salmon et al. |
| 5,320,602 A | 6/1994 | Karpiel |
| 5,324,259 A | 6/1994 | Taylor et al. |
| 5,324,269 A | 6/1994 | Miraki |
| 5,328,472 A | 7/1994 | Steinke et al. |
| 5,334,143 A | 8/1994 | Carroll |
| 5,334,147 A | 8/1994 | Johnson |
| 5,334,187 A | 8/1994 | Fischell et al. |
| 5,336,184 A | 8/1994 | Teirstein |
| 5,338,313 A | 8/1994 | Mollenauer et al. |
| 5,342,297 A | 8/1994 | Jang |
| 5,346,498 A | 9/1994 | Greelis et al. |
| 5,350,395 A | 9/1994 | Yock |
| 5,352,215 A | 10/1994 | Thome et al. |
| 5,354,280 A | 10/1994 | Haber et al. |
| 5,357,978 A | 10/1994 | Turk |
| 5,364,355 A | 11/1994 | Alden et al. |
| 5,364,376 A | 11/1994 | Horzewski et al. |
| 5,368,567 A | 11/1994 | Lee |
| 5,370,623 A | 12/1994 | Kreamer |
| 5,380,283 A | 1/1995 | Johnson |
| 5,385,552 A | 1/1995 | Haber et al. |
| 5,387,226 A | 2/1995 | Miraki |
| 5,389,087 A | 2/1995 | Miraki |
| 5,389,100 A | 2/1995 | Bacich et al. |
| 5,391,153 A | 2/1995 | Haber et al. |
| 5,395,335 A | 3/1995 | Jang |
| 5,395,342 A | 3/1995 | Yoon |
| 5,397,302 A | 3/1995 | Weaver et al. |
| 5,397,335 A | 3/1995 | Gresl et al. |
| 5,407,433 A | 4/1995 | Loomas |
| 5,409,459 A | 4/1995 | Gambale |
| 5,413,559 A | 5/1995 | Sirhan et al. |
| 5,415,633 A | 5/1995 | Lazarus et al. |
| 5,415,639 A | 5/1995 | VandenEinde et al. |
| 5,441,486 A | 8/1995 | Yoon |
| 5,448,993 A | 9/1995 | Lynch et al. |
| 5,449,363 A | 9/1995 | Brust et al. |
| 5,451,233 A | 9/1995 | Yock |
| 5,454,790 A | 10/1995 | Dubrul |
| 5,458,584 A | 10/1995 | Ginn et al. |
| 5,458,605 A | 10/1995 | Klemm |
| 5,460,168 A | 10/1995 | Masubuchi et al. |
| 5,462,530 A | 10/1995 | Jang |
| 5,480,389 A | 1/1996 | McWha et al. |
| 5,489,271 A | 2/1996 | Andersen |
| 5,490,837 A | 2/1996 | Blaeser et al. |
| 5,490,859 A | 2/1996 | Mische et al. |

(56) References Cited

U.S. PATENT DOCUMENTS

| | | | |
|---|---|---|---|
| 5,496,346 A | 3/1996 | Horzewski et al. |
| 5,501,227 A | 3/1996 | Yock |
| 5,531,700 A | 7/1996 | Moore et al. |
| 5,536,234 A | 7/1996 | Newman |
| 5,536,248 A | 7/1996 | Weaver et al. |
| 5,540,236 A | 7/1996 | Ginn |
| 5,547,469 A | 8/1996 | Rowland et al. |
| 5,599,299 A | 2/1997 | Weaver et al. |
| 5,599,300 A | 2/1997 | Weaver et al. |
| 5,605,162 A | 2/1997 | Mirzaee et al. |
| 5,613,949 A | 3/1997 | Miraki |
| 5,626,600 A | 5/1997 | Horzewski et al. |
| 5,634,475 A | 6/1997 | Wolvek |
| 5,637,086 A | 6/1997 | Ferguson et al. |
| 5,645,519 A | 7/1997 | Lee et al. |
| 5,685,853 A | 11/1997 | Bonnet |
| 5,693,015 A | 12/1997 | Walker et al. |
| 5,706,827 A | 1/1998 | Ehr et al. |
| 5,707,363 A | 1/1998 | Crawford et al. |
| 5,709,658 A | 1/1998 | Sirhan et al. |
| 5,718,680 A | 2/1998 | Kraus et al. |
| 5,725,504 A | 3/1998 | Collins |
| 5,743,884 A * | 4/1998 | Hasson ............ A61B 17/3462 137/247.17 |
| 5,755,695 A | 5/1998 | Erickson et al. |
| 5,765,682 A | 6/1998 | Bley et al. |
| 5,788,681 A | 8/1998 | Weaver et al. |
| 5,800,414 A | 9/1998 | Cazal |
| 5,820,600 A | 10/1998 | Carlson et al. |
| 5,823,995 A | 10/1998 | Fitzmaurice et al. |
| 5,833,706 A | 11/1998 | St. Germain et al. |
| 5,836,306 A | 11/1998 | Duane et al. |
| 5,843,028 A | 12/1998 | Weaver et al. |
| 5,849,016 A | 12/1998 | Suhr |
| 5,851,189 A | 12/1998 | Forber |
| 5,891,056 A | 4/1999 | Ramzipoor |
| 5,919,004 A | 7/1999 | Christenson |
| 5,921,971 A | 7/1999 | Agro et al. |
| 5,931,833 A | 8/1999 | Silverstein |
| 5,935,114 A | 8/1999 | Jang et al. |
| 5,978,699 A | 11/1999 | Fehse et al. |
| 6,007,522 A | 12/1999 | Agro et al. |
| 6,053,861 A | 4/2000 | Grossi |
| RE36,702 E | 5/2000 | Green et al. |
| 6,093,176 A | 7/2000 | Dennis |
| 6,096,009 A | 8/2000 | Windheuser et al. |
| 6,106,487 A | 8/2000 | Duane et al. |
| 6,152,910 A | 11/2000 | Agro et al. |
| 6,190,333 B1 | 2/2001 | Valencia |
| 6,190,358 B1 | 2/2001 | Fitzmaurice et al. |
| 6,200,262 B1 | 3/2001 | Ouchi |
| 6,245,437 B1 | 6/2001 | Shiiki et al. |
| 6,254,529 B1 | 7/2001 | Ouchi |
| 6,277,100 B1 | 8/2001 | Raulerson et al. |
| 6,312,404 B1 | 11/2001 | Agro et al. |
| 6,322,577 B1 | 11/2001 | McInnes |
| 6,346,093 B1 | 2/2002 | Allman et al. |
| 6,517,518 B2 | 2/2003 | Nash et al. |
| 6,520,951 B1 | 2/2003 | Carrillo, Jr. et al. |
| 6,582,401 B1 | 6/2003 | Windheuser et al. |
| 6,595,946 B1 * | 7/2003 | Pasqualucci ....... A61B 17/3462 604/164.01 |
| 6,606,515 B1 | 8/2003 | Windheuser et al. |
| 6,607,529 B1 | 8/2003 | Jones et al. |
| 6,663,597 B1 | 12/2003 | Windheuser et al. |
| 6,663,598 B1 | 12/2003 | Carrillo, Jr. et al. |
| 6,679,872 B2 | 1/2004 | Turovskiy et al. |
| 6,746,442 B2 | 6/2004 | Agro et al. |
| 6,746,466 B2 | 6/2004 | Eidenschink et al. |
| 6,764,484 B2 | 7/2004 | Richardson et al. |
| D498,992 S | 11/2004 | Bloom |
| 6,827,683 B2 | 12/2004 | Otawara |
| 6,827,718 B2 | 12/2004 | Hutchins et al. |
| 6,851,424 B2 | 2/2005 | Scopton |
| 6,863,661 B2 | 3/2005 | Carrillo, Jr. et al. |
| 6,869,416 B2 | 3/2005 | Windheuser et al. |
| 6,879,854 B2 | 4/2005 | Windheuser et al. |
| 6,893,393 B2 | 5/2005 | Carrillo |
| 6,925,323 B2 | 8/2005 | Snoke |
| 6,997,908 B2 | 2/2006 | Carrillo, Jr. et al. |
| 7,009,837 B2 | 3/2006 | Lo |
| 7,037,293 B2 | 5/2006 | Carrillo et al. |
| 7,060,052 B2 | 6/2006 | Windheuser et al. |
| 7,076,285 B2 | 7/2006 | Windheuser et al. |
| 7,160,283 B2 | 1/2007 | Richardson et al. |
| 7,172,577 B2 | 2/2007 | Mangano et al. |
| 7,178,520 B2 | 2/2007 | Scopton |
| 7,179,252 B2 | 2/2007 | Agro et al. |
| 7,226,411 B2 | 6/2007 | Akiba |
| 7,473,221 B2 | 1/2009 | Ewers et al. |
| 7,637,863 B2 | 12/2009 | Deal et al. |
| 7,670,285 B2 | 3/2010 | Yamaya |
| 7,670,316 B2 | 3/2010 | Windheuser et al. |
| 7,803,107 B2 | 9/2010 | Carrillo |
| 7,967,744 B2 | 6/2011 | Kaye et al. |
| 8,152,774 B2 | 4/2012 | Pasqualucci |
| 8,231,525 B2 | 7/2012 | Cohen et al. |
| 8,333,693 B2 | 12/2012 | Hamazaki |
| 8,343,041 B2 | 1/2013 | Byers et al. |
| 8,388,521 B2 * | 3/2013 | Byers .................. A61B 1/018 600/154 |
| 8,480,570 B2 | 7/2013 | Tinkham et al. |
| 8,647,256 B2 | 2/2014 | Carrillo, Jr. |
| 8,702,596 B2 | 4/2014 | Kaye et al. |
| 8,753,264 B2 | 6/2014 | Carrillo, Jr. et al. |
| 8,974,377 B2 | 3/2015 | Yamane |
| 9,089,261 B2 | 7/2015 | Greenburg et al. |
| 9,101,738 B2 | 8/2015 | Eden |
| 9,131,831 B2 | 9/2015 | Byers et al. |
| 9,622,776 B2 | 4/2017 | Oberlaender et al. |
| 9,986,895 B2 | 6/2018 | Meloul |
| 2001/0029362 A1 | 10/2001 | Sirhan et al. |
| 2002/0007152 A1 | 1/2002 | Hermann et al. |
| 2002/0016612 A1 | 2/2002 | Ashby et al. |
| 2003/0088153 A1 | 5/2003 | Carrillo, Jr. et al. |
| 2003/0208104 A1 | 11/2003 | Carrillo, Jr. et al. |
| 2003/0233043 A1 | 12/2003 | Windheuser et al. |
| 2004/0106852 A1 | 6/2004 | Windheuser et al. |
| 2004/0111060 A1 | 6/2004 | Racenet et al. |
| 2004/0162465 A1 | 8/2004 | Carrillo |
| 2004/0193142 A1 | 9/2004 | Agro et al. |
| 2005/0059890 A1 | 3/2005 | Deal et al. |
| 2005/0090835 A1 | 4/2005 | Deal et al. |
| 2005/0148820 A1 | 7/2005 | Carrillo |
| 2005/0165277 A1 | 7/2005 | Carrillo, Jr. et al. |
| 2005/0203543 A1 | 9/2005 | Hilal et al. |
| 2006/0135978 A1 | 6/2006 | Franer |
| 2006/0142734 A1 | 6/2006 | Carrillo, Jr. et al. |
| 2006/0195117 A1 | 8/2006 | Rucker et al. |
| 2006/0229496 A1 | 10/2006 | Windheuser et al. |
| 2006/0287578 A1 * | 12/2006 | Hamazaki .......... A61B 1/00137 600/154 |
| 2007/0238928 A1 | 10/2007 | Maseda et al. |
| 2007/0244356 A1 | 10/2007 | Carrillo, Jr. et al. |
| 2007/0282166 A1 | 12/2007 | Ayala et al. |
| 2007/0293719 A1 | 12/2007 | Scopton et al. |
| 2008/0194913 A1 | 8/2008 | Tinkham et al. |
| 2008/0249362 A1 | 10/2008 | Jiang et al. |
| 2008/0290605 A1 * | 11/2008 | Brockmeier ....... A61B 17/3462 277/355 |
| 2009/0076464 A1 | 3/2009 | Gresham |
| 2010/0087705 A1 * | 4/2010 | Byers ................... A61M 39/06 600/104 |
| 2010/0240956 A1 | 9/2010 | Secrest et al. |
| 2012/0071713 A1 | 3/2012 | Kaye et al. |
| 2013/0144117 A1 | 6/2013 | Byers et al. |
| 2016/0206859 A1 | 7/2016 | Eden |

FOREIGN PATENT DOCUMENTS

| | | |
|---|---|---|
| CN | 105816208 A | 8/2016 |
| CN | 205697867 U | 11/2016 |
| DE | 4115007 A1 | 11/1992 |

(56) References Cited

FOREIGN PATENT DOCUMENTS

| | | | |
|---|---|---|---|
| DE | 19911911 A1 | 9/1999 |
| DE | 19916866 A1 | 10/1999 |
| EP | 0328760 A2 | 8/1989 |
| EP | 0388112 A1 | 9/1990 |
| EP | 0792657 A2 | 9/1997 |
| EP | 0801955 B1 | 3/1999 |
| EP | 1779764 A1 | 5/2007 |
| EP | 1997444 A2 | 12/2008 |
| EP | 1406691 B1 | 1/2010 |
| EP | 2323540 A1 | 5/2011 |
| EP | 2564758 A1 | 3/2013 |
| EP | 2574271 A1 | 4/2013 |
| EP | 2020901 B1 | 7/2016 |
| JP | 50108287 U | 9/1975 |
| JP | 3126428 A | 5/1991 |
| JP | 623055 A | 2/1994 |
| JP | 7155382 A | 6/1995 |
| JP | 994253 A | 4/1997 |
| JP | 2008123063 A | 5/2008 |
| JP | 2009268777 A | 11/2009 |
| WO | 9203963 A1 | 3/1992 |
| WO | 9613296 A1 | 5/1996 |
| WO | 96633764 A1 | 10/1996 |
| WO | 9810820 A1 | 3/1998 |
| WO | 9810821 A1 | 3/1998 |
| WO | 9938557 A1 | 8/1999 |
| WO | 9959664 A1 | 11/1999 |
| WO | 0069499 A1 | 11/2000 |
| WO | 0069500 A1 | 11/2000 |
| WO | 2008101286 A1 | 8/2008 |

OTHER PUBLICATIONS

Knecht, Gregory L., M.D. et al., "Double-Channel Fismlotome for Endoscopic Drainage of Pancreatic Pseudocyst," Gastrointestinal Endoscopy, 37(3): May/Jun. 1991, pp. 356-357.

Siegel, Jerome H., M.D. et al., "Two New Methods for Selective Bile Duct Cannulation and Sphincterotomy," Gastrointestinal Endoscopy, 33(6): Dec. 1987, pp. 438-440.

International Search Report and Written Opinion dated Nov. 14, 2018 for International Application No. PCT/US2018/046280.

* cited by examiner

BIOPSY CAP FOR USE WITH ENDOSCOPE

RELATED APPLICATION

This application claims the benefit of U.S. Provisional Application Ser. No. 62/544,581 entitled BIOPSY CAP FOR USE WITH ENDOSCOPE, which application is incorporated by reference herein in its entirety.

TECHNICAL FIELD

The present disclosure pertains to endoscopes, endoscope assemblies, guidetubes, introducers, and instrument caps for endoscopes, guidetubes, and introducers. More particularly, the present disclosure pertains to biopsy caps for an access port of an endoscope.

BACKGROUND

A wide variety of endoscope assemblies and biopsy caps have been developed. Of the known endoscope assemblies and biopsy caps, each has certain advantages and disadvantages. There is an ongoing need to provide alternative endoscope assemblies and biopsy caps as well as methods for making and using the same.

SUMMARY

The invention provides design, material, and manufacturing method alternatives for endoscope assemblies and biopsy caps as well as provides methods for making and using endoscope assemblies and biopsy caps. An example of the disclosure is a biopsy cap for use with an endoscopic instrument. The biopsy cap includes a base having a securing member for securing the biopsy cap to a port on the endoscopic instrument as well as an outer shell that is securable to the base and that defines an interior volume. A disk shutter section is disposed within the interior volume and includes a plurality of fins arranged in a helical fashion. A brush section is disposed within the interior volume adjacent the disk shutter section and includes a plurality of brushes arranged in a helical fashion.

Alternatively or additionally to any embodiment above, the biopsy cap may further include a locking member coupled to the outer shell.

Alternatively or additionally to any embodiment above, the disk shutter section may include a central aperture extending axially therethrough and the plurality of fins may be adapted to bend away from the central aperture in response to an elongate member being passed through the disk shutter section but are biased towards the elongate member.

Alternatively or additionally to any embodiment above, the elongate member may include a C-shaped channel, and at least some of the plurality of fins may be adapted to extend into the C-shaped channel to at least partially block fluid flow through the biopsy cap along the C-shaped channel.

Alternatively or additionally to any embodiment above, the brush section may include a central aperture extending axially therethrough and the plurality of brushes may be adapted to bend away from the central aperture in response to an elongate member being passed through the brush section, but are biased towards the elongate member.

Alternatively or additionally to any embodiment above, the elongate member may include a C-shaped channel, and at least some of the plurality of brushes may be adapted to extend into the C-shaped channel to at least partially block fluid flow through the biopsy cap along the C-shaped channel.

Alternatively or additionally to any embodiment above, the brush section may include a plurality of individual brush layers stacked together, where each individual brush layer includes an annular outer ring several of the plurality of brushes, each secured to the outer annular ring and extending towards a center point of the individual brush layer, each radially spaced apart along the outer annular ring and each individual brush layer rotated relative to adjacent individual brush layers such that the plurality of brushes are arranged in a helix.

Alternatively or additionally to any embodiment above, the brush section may include a plurality of brush section portions that are individually molded and then adhered together to form the brush section.

Alternatively or additionally to any embodiment above, the brush section may be molded as a linear shape having a first end and a second end, and the first end and the second end are subsequently joined together to form the brush section.

Alternatively or additionally to any embodiment above, the brush section may include a plurality of brush layers that are secured to each other and sequentially folded together to form the brush section.

Alternatively or additionally to any embodiment above, the biopsy cap may further include a hydrophilic foam section disposed within the interior volume adjacent the brush section.

In another example, a biopsy cap for use with an endoscopic instrument includes a base having a securing member for securing the biopsy cap to a port on the endoscopic instrument as well as an outer shell that is securable to the base and that defines an interior volume. A brush section is disposed within the interior volume adjacent the disk shutter section and includes a plurality of brushes arranged in a helical fashion. A hydrophilic foam section is disposed within the interior volume adjacent the brush section.

Alternatively or additionally to any embodiment above, the biopsy cap may further include a disk shutter section that is disposed within the interior volume and that includes a plurality of fins arranged in a helical fashion, the disk shutter section disposed adjacent the brush section.

Alternatively or additionally to any embodiment above, the brush section may include a central aperture extending axially therethrough and the plurality of brushes may be adapted to bend away from the central aperture in response to an elongate member being passed through the brush section, but are biased towards the elongate member.

Alternatively or additionally to any embodiment above, the elongate member may include a C-shaped channel, and at least some of the plurality of brushes may be adapted to extend into the C-shaped channel to at least partially block fluid flow through the biopsy cap along the C-shaped channel.

Alternatively or additionally to any embodiment above, the brush section may include a plurality of individual brush layers.

Alternatively or additionally to any embodiment above, each individual brush layer may include an outer annular ring and several of the plurality of brushes, each secured to the outer annular ring and extending towards a center point of the individual brush layer, each radially spaced apart along the outer annular ring.

Alternatively or additionally to any embodiment above, each of the individual brush layers may be stacked together, with each individual brush layer rotated relative to adjacent individual brush layers such that the plurality of brushes are arranged in a helix.

Alternatively or additionally to any embodiment above, the plurality of individual brush layers may be adhesively secured together.

In another example, a biopsy cap for use with an endoscopic instrument includes a base having a securing member for securing the biopsy cap to a port on the endoscopic instrument, the base including an aperture to accommodate an elongate member extendable through the biopsy cap. An outer shell is securable to the base and defines an interior volume, the outer shell including an aperture to accommodate the elongate member extendable through the biopsy cap. A disk shutter section is disposed within the interior volume and includes a plurality of fins that are arranged in a helical fashion and that extend towards an aperture to accommodate the elongate member. A brush section is disposed within the interior volume adjacent the disk shutter section, the brush section including a plurality of brushes arranged in a helical fashion, the plurality of brushes extending towards an aperture to accommodate the elongate member.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
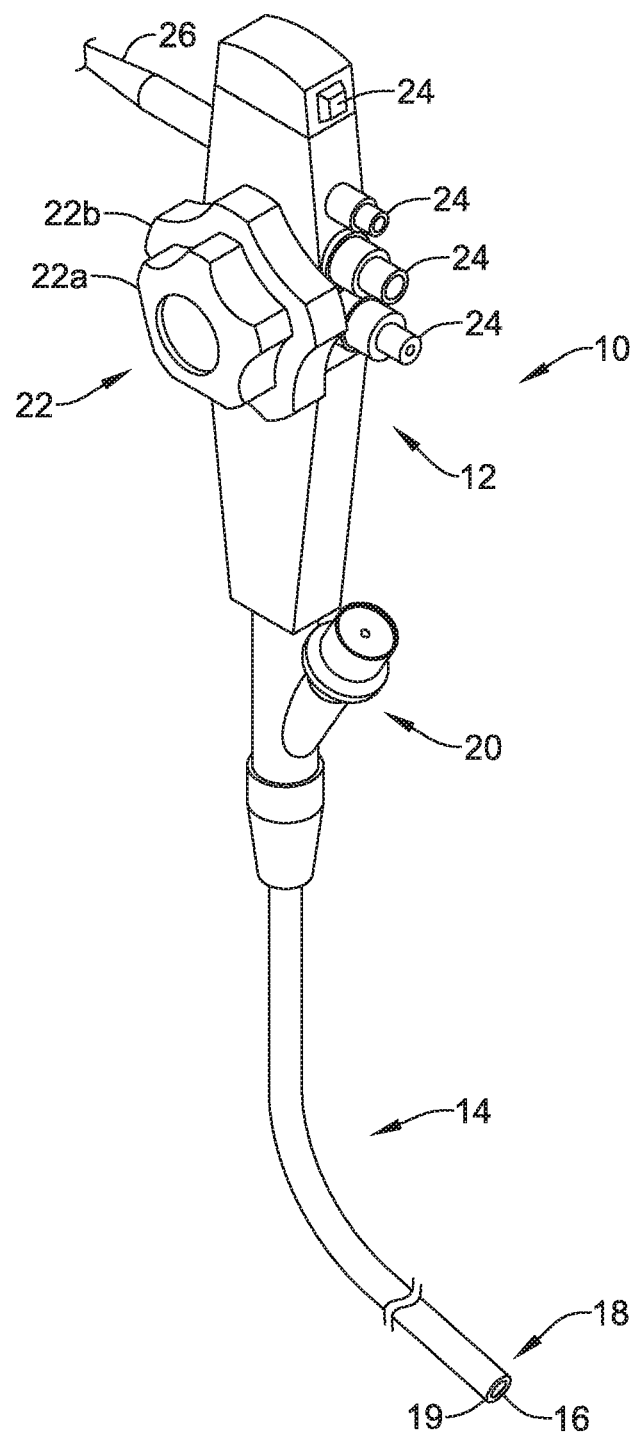
FIG. 1 is a perspective view of an example endoscope assembly.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

An example endoscope and/or endoscope assembly 10 is illustrated in FIG. 1. The endoscope 10 may be any of a number of types of endoscopes or related medical devices usually identified by the particular anatomy desired to be reached. For example, the endoscope 10 may be a bronchoscope, colonoscope, duodenoscope, esophagoscope, guidetubes, introducers (without or without vision or visualization capabilities), or any other type of endoscope or related medical device. The endoscope 10 may include a handpiece 12 and an elongate shaft 14 extending distally from the handpiece 12 to a distal tip 18. The shaft 14 may include a lumen defining a working channel 16 extending through the shaft 14 from a distal end 19 near the distal tip 18 of shaft 14 to an access port 20 that may be positioned in the handpiece 12 or another portion of the endoscope 10. Although the endoscope 10 is depicted with a single working channel in FIG. 1, it can be appreciated that in other embodiments, the endoscope 10 may include multiple working channels, as desired.

In some cases, the handpiece 12 may include one or a plurality of controls 22, such as rotating knobs, which may be used to control movement of the distal tip 18 of the shaft 14 during operation. For example, a first rotating knob 22*a* may control up and down movement or deflection of the distal tip 18 of the shaft 14, while a second rotating knob 22*b* may control side-to-side movement or deflection of the distal tip 18 of the shaft 14. The handpiece 12 may also include one or a plurality of buttons 24, which may be used to activate suction or deliver fluid such as air, saline and/or water, etc. through a lumen of the endoscope 10 or perform other functions as desired. Additionally, in some cases, the handpiece 12 may include an optical cable 26 connected to an external light source (not shown).

Figure 2:
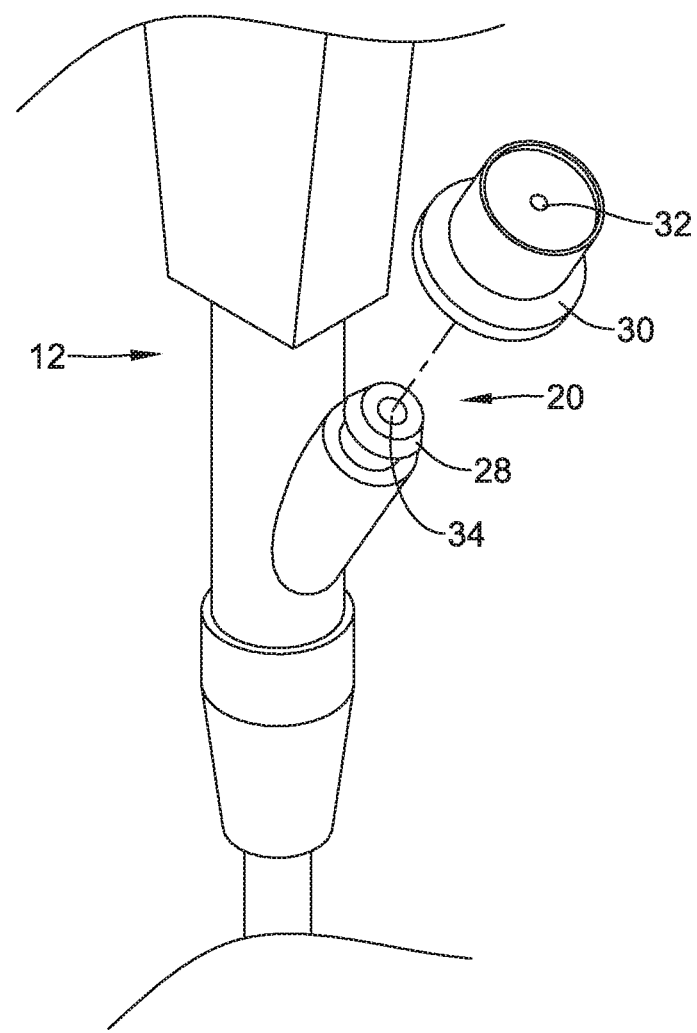
FIG. 2 is an exploded view of a portion of the example endoscope assembly shown in FIG. 1 illustrating a biopsy cap.

Turning now to FIG. 2, here the access port 20 of the handpiece 12, which provides access to the working channel 16 of the endoscope 10, is illustrated. The access port 20, which may extend from the side of the endoscope 10 or at another location, may include a coupling portion 28 for coupling a cap 30 to the access port 20. The cap 30, which may be removably attached or permanently attached to the access port 20, may provide access for inserting and/or advancing an endoscopic device through working channel 16 of endoscope 10. It will be appreciated that the cap 30 shown in FIG. 1 is intended to be merely illustrative, as the cap 30 may take a variety of different exterior profiles as will be shown in subsequent Figures.

In some cases, caps like cap 30, which may be termed "biopsy caps", may be designed with several functions in mind. For example, the cap 30 may form a fluid/air barrier to the working channel 16 that may help control insufflation and bile fluid egress therefrom that later have the potential to spill onto the clinician's hands and/or the floor thereby interfering with the intervention and/or become a biohazard. In addition, the cap 30 may have an opening 32 extending therethrough. The opening 32 may be in fluid communication with the working channel 16 and it may reduce the size of the opening 34 of working channel 16, for example, to accommodate an endoscopic device or instrument. Thus, caps like cap 30 may be much like an adapter in that it forms a physical transition at opening 34 of working channel 16 (or other instrument channels or access points) so that it transitions to a size more closely to that of the device to be inserted into working channel 16.

A number of additional biopsy caps are contemplated that incorporate at least some of the desirable features of biopsy caps as well as have other desirable characteristics. The forgoing discussion discloses some of the embodiments of caps that are contemplated. These caps may include a passive seal. For the purposes of this disclosure, a passive seal is a seal that seals the endoscope 10 at the port 20 so as to prevent the leakage of bodily fluids and/or air. In addition, by virtue of being "passive", the caps disclosed herein are configured to seal off the endoscope 10 at the port 20 without the need of any so-called "active" processes or steps by the clinician.

Figure 3:
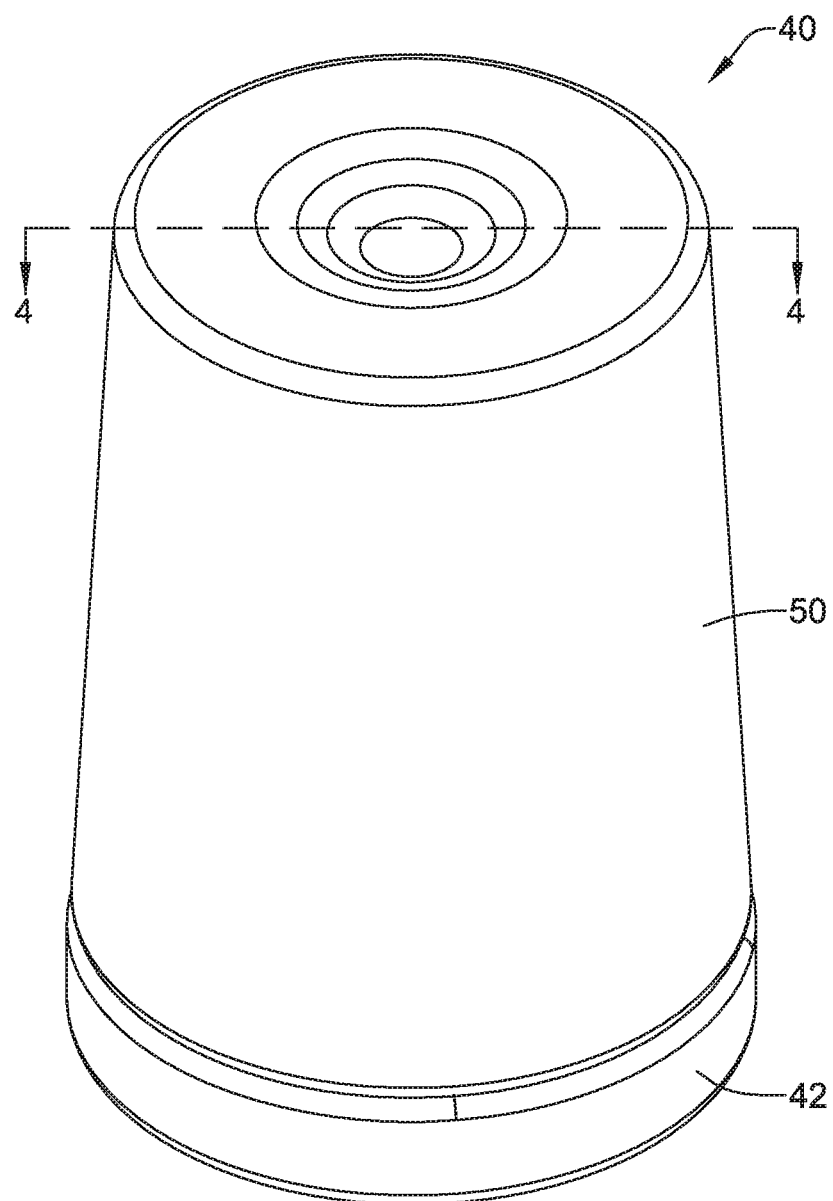
FIG. 3 is a perspective view of an example biopsy cap that may be used in combination with the endoscope assembly of FIG. 1.
Figure 4:
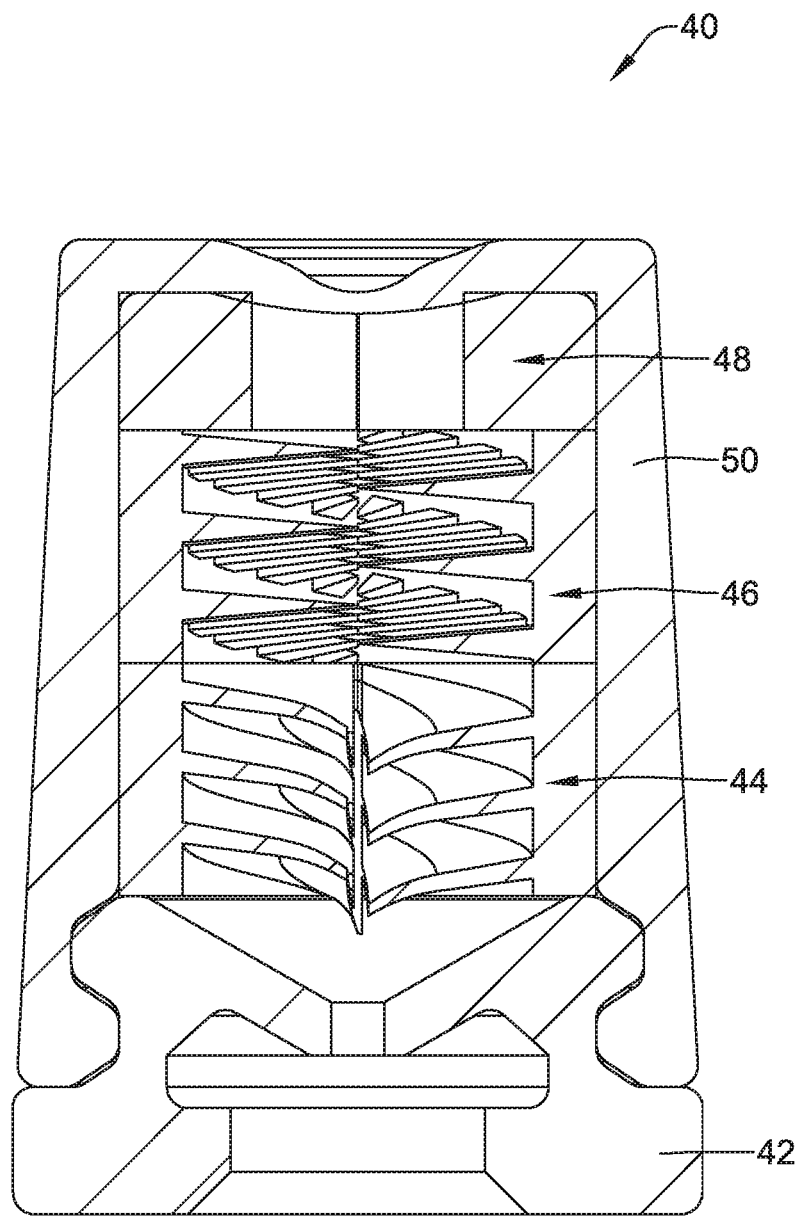
FIG. 4 is a cross-sectional view of the biopsy cap of FIG. 1, taken along the line 4-4.
Figure 5:
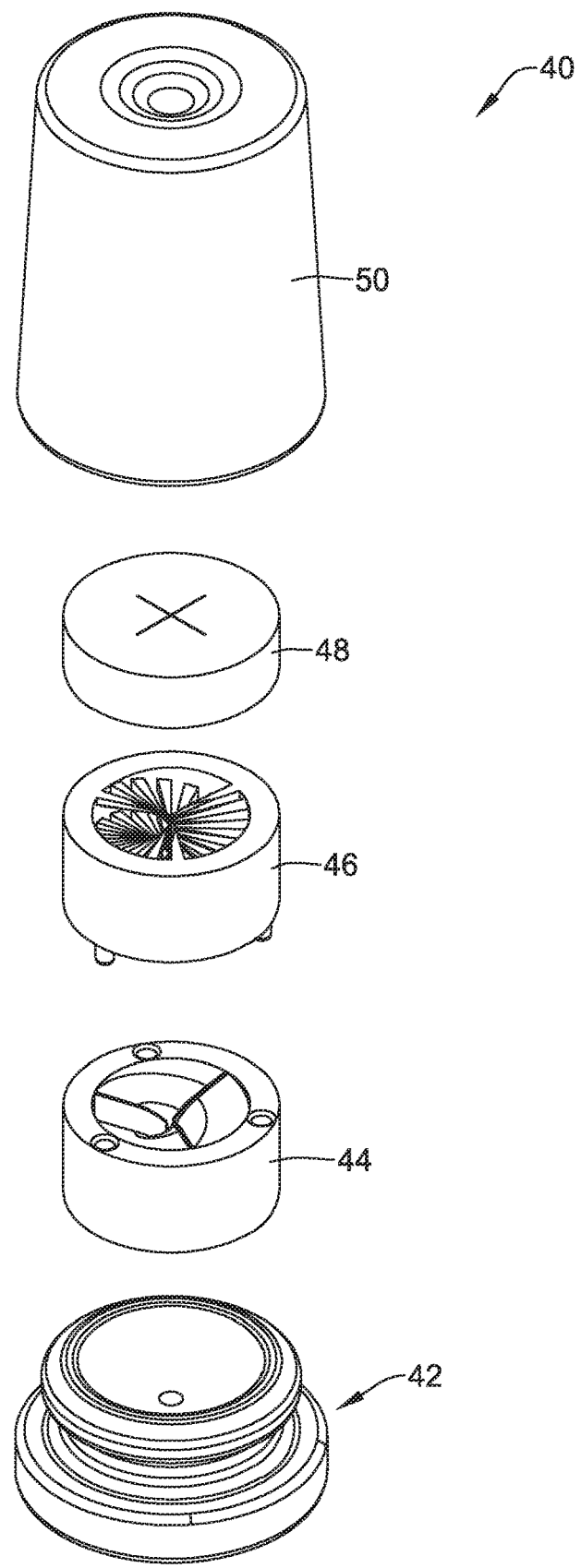
FIG. 5 is an exploded perspective view of the biopsy cap of FIG. 1.

FIG. 3 is a perspective view of a biopsy cap 40 that may, for example, be used in place of the cap 30 shown in FIGS. 1 and 2. FIG. 4 is a cross-sectional view of the biopsy cap 40, taken along the line 4-4 while FIG. 5 is an exploded view further illustrating the individual components included within the biopsy cap 40. The biopsy cap 40 includes a base 42, a disk shutter section 44, a brush section 46, a foam section 48 and an outer shell 50. In some cases, as illustrated, the disk shutter section 44 is at the bottom, with the brush section 46 disposed above the disk shutter section 44 and the foam section 48 disposed above the brush section 46. As can be seen, the outer shell 50 is connectable to the base 42, and defines an interior volume (best illustrated in FIG. 6B) into which the disk shutter section 44, the brush section 46 and the foam section 48 fit. It will be appreciated that the biopsy cap 40 is configured to accommodate one or more elongate members, such as but not limited to catheters and guidewires, extending through the biopsy cap 40 while limiting or even preventing fluid flow through the biopsy cap 40. Each of the individual components of the biopsy cap 40 will be discussed in greater detail with respect to subsequent Figures.

Figure 6A:
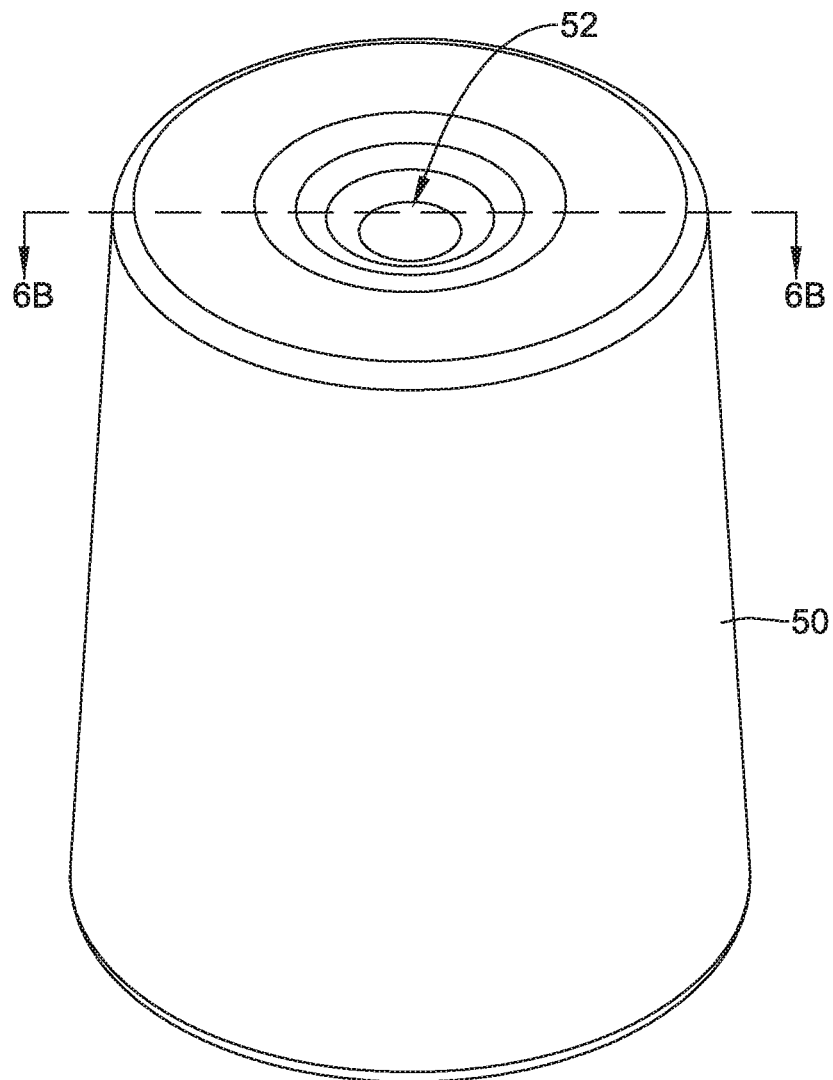
FIG. 6A is a perspective view of an outer shell forming a portion of the biopsy cap of FIG. 1.
Figure 6B:
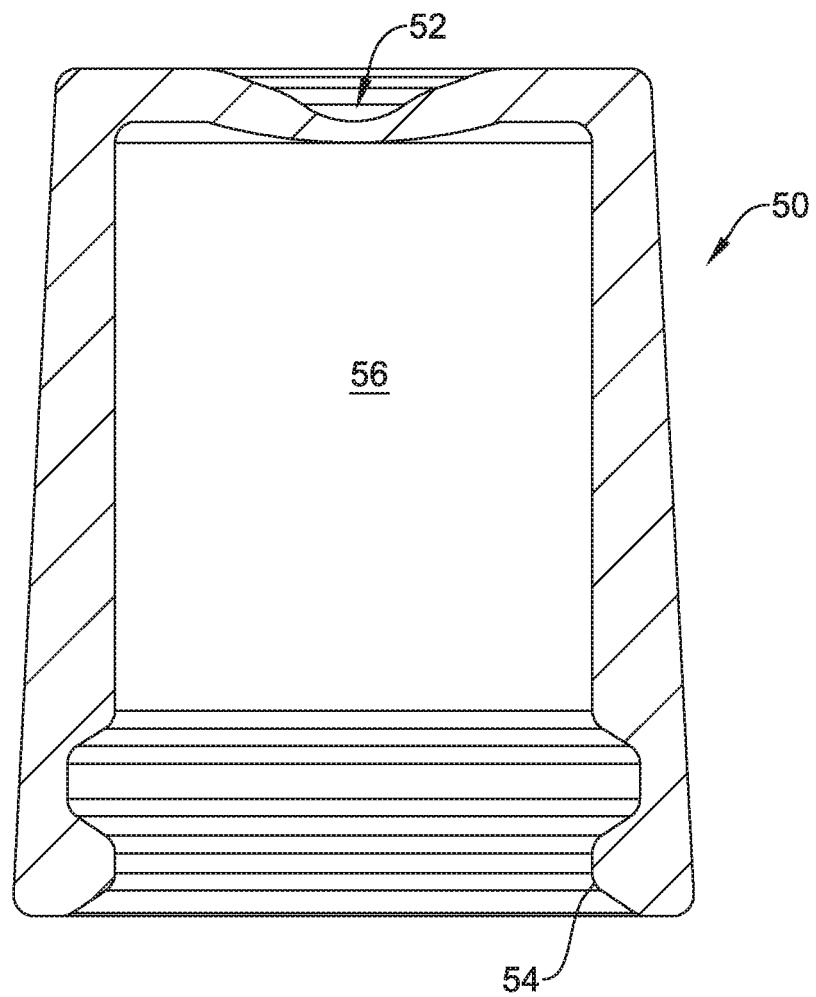
FIG. 6B is a cross-sectional view of the outer shell of FIG. 6A, taken along the line 6-6.

FIG. 6A is a perspective view of the outer shell 50 while FIG. 6B is a cross-sectional view, taken along the line 6-6, of the outer shell 50. As illustrated, the outer shell 50 has a tapered overall profile, but in some cases the outer shell 50 may have a more cylindrical profile, for example. In other cases, the outer shell 50 may have an ovoid or a rectilinear profile, if desired. The outer shell 50 includes an outer shell aperture 52 in order to accommodate an elongate member extending therethrough. In some cases, as illustrated, the outer shell 50 includes a securement feature 54 that may be contoured to provide a frictional fit with a corresponding securement feature disposed relative to the base 42 (as will be discussed with respect to subsequent Figures). As can be seen, the outer shell 50 defines an interior volume 56, into which the disk shutter section 44, the brush section 46 and the foam section 48 may be disposed. The outer shell 50 may be formed of any suitable materials, such as the silicone materials available commercially under the ELASTOSIL™ name. In some cases, the outer shell 50 may be formed of LSR Silicone having a Shore Hardness of 40 or 50.

Figure 7A:
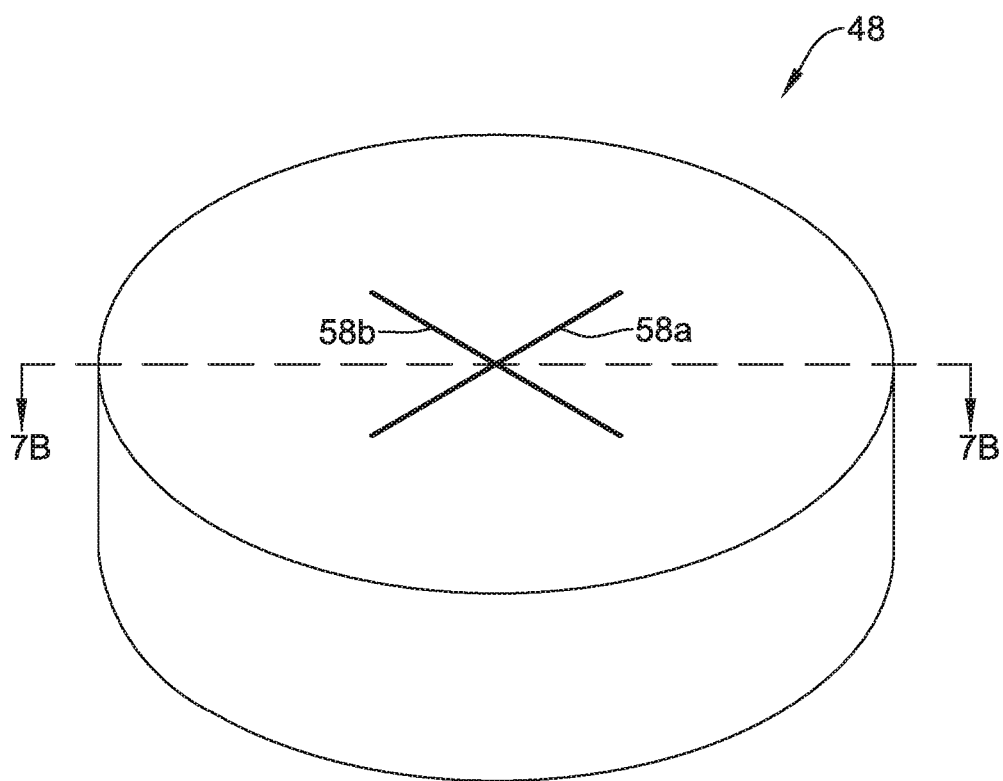
FIG. 7A is a perspective view of a foam member forming a portion of the biopsy cap of FIG. 1.
Figure 7B:
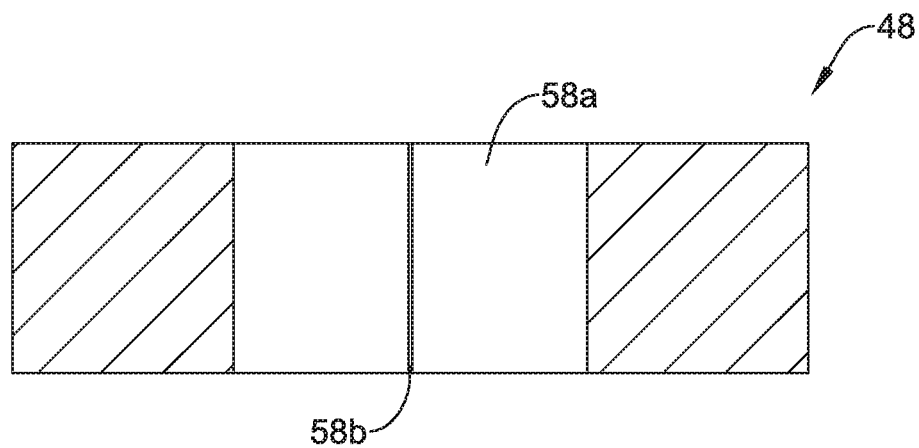
FIG. 7B is a cross-sectional view of the foam member of FIG. 7A, taken along the line 7-7.

FIG. 7A is a perspective view of the foam section 48 while FIG. 7B is a cross-sectional view, taken along the line 7-7, of the foam section 48. In some cases, the foam section 48 may be formed of a hydrophilic foam such as but not limited to a polyurethane foam. As illustrated, the foam section 48 has a cylindrical profile, in order to fit within the interior volume 56 of the outer shell 50. In some cases, if the outer shell 50 has a different profile, the foam section 48 may have a complementary profile. The foam section 48 may be configured to accommodate an elongate member extending therethrough via a pair of cuts 58a, 58b. In some cases, the cuts 58a, 58b are orthogonal to each other. FIG. 7B is a cross-sectional view through the cut 58a, showing the cut 58b as having a cut thickness. In some cases, the cuts 58a, 58b each have a cut thickness of about 0.002 inches, although this is just an example. It will be appreciated that as an elongate member is extended through the foam section 48, the material forming the foam section 48 will deform to let the elongate member extend through, but will be biased into contact with the elongate member in order to help block fluid flow through the biopsy cap 40.

Figure 8A:
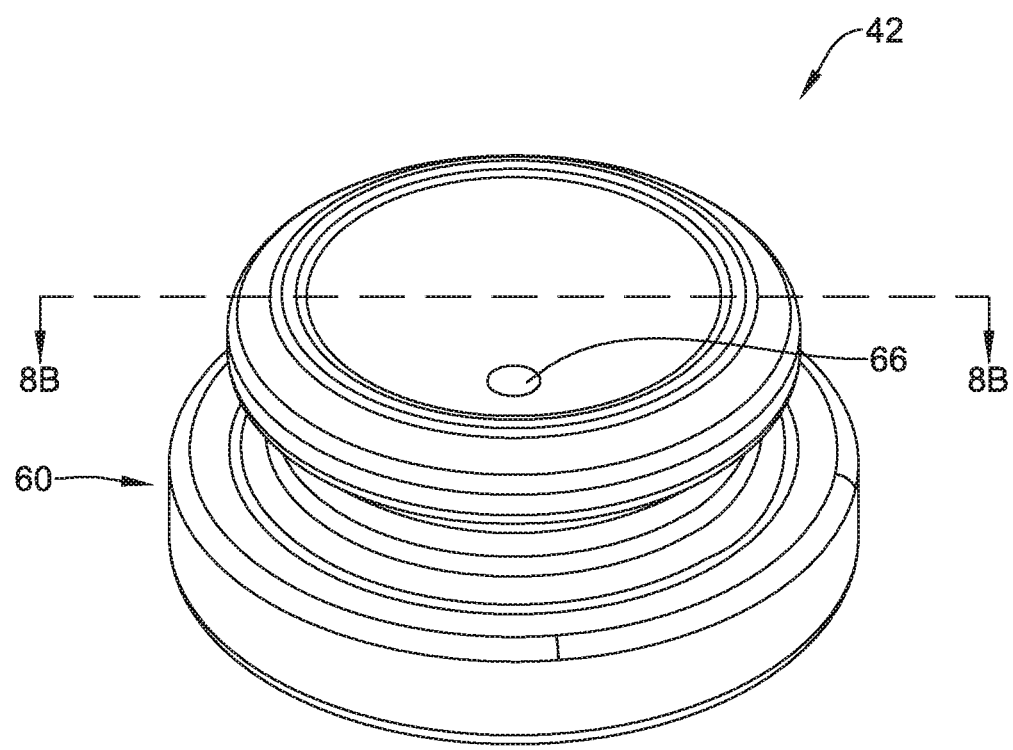
FIG. 8A is a perspective view of a base forming a portion of the biopsy cap of FIG. 1.
Figure 8B:
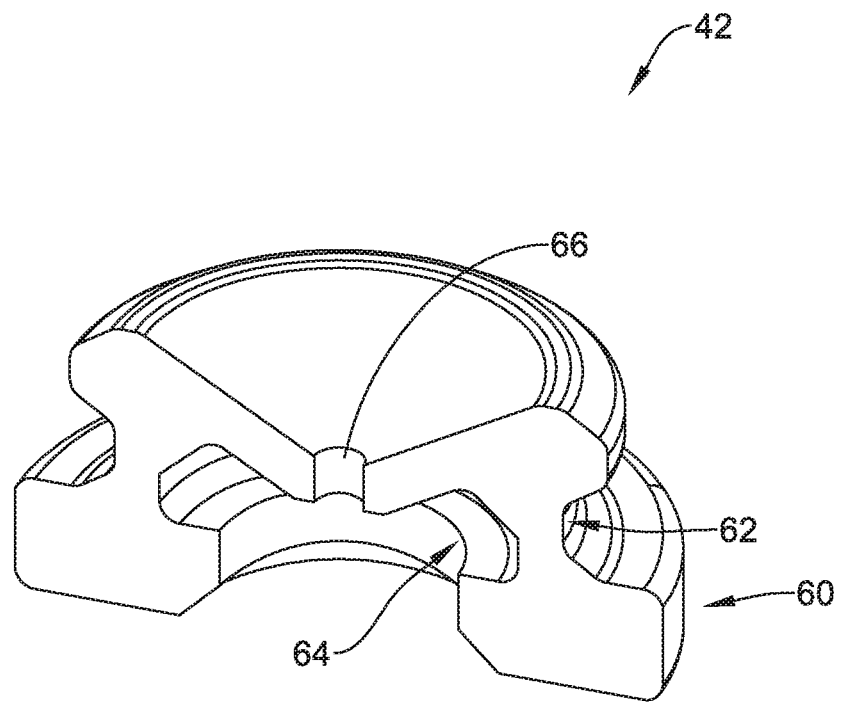
FIG. 8B is a cross-sectional view of the base of FIG. 8A, taken along the line 8-8.

FIG. 8A is a perspective view of the base 42 while FIG. 8B is a cross-sectional view, taken along the line 8-8, of the base 42. The base 42 includes a body 60 defining a recessed annular portion 62. It will be appreciated that the recessed annular portion 62 is complementary to the securement feature 54 formed as part of the outer shell 50, and thus the outer shell 50 may be secured to the base 42 via a frictional fit. In some cases, the base 42 and/or the outer shell 50 may be formed of a sufficiently flexible material in order to enable the outer shell 50 to be snapped into position on the base 42. The body 60 also defines a securement region 64 that may be configured to frictionally engage the port 20 (FIG. 2). An aperture 66 extends through the body 60 in order to accommodate an elongate member extending through the biopsy cap 40. The base 42 may be formed of any suitable materials, such as the silicone materials available commercially under the ELASTOSIL™ name. In some cases, the base 42 may be formed of LSR Silicone having a Shore Hardness of 40 or 50.

Figure 9A:
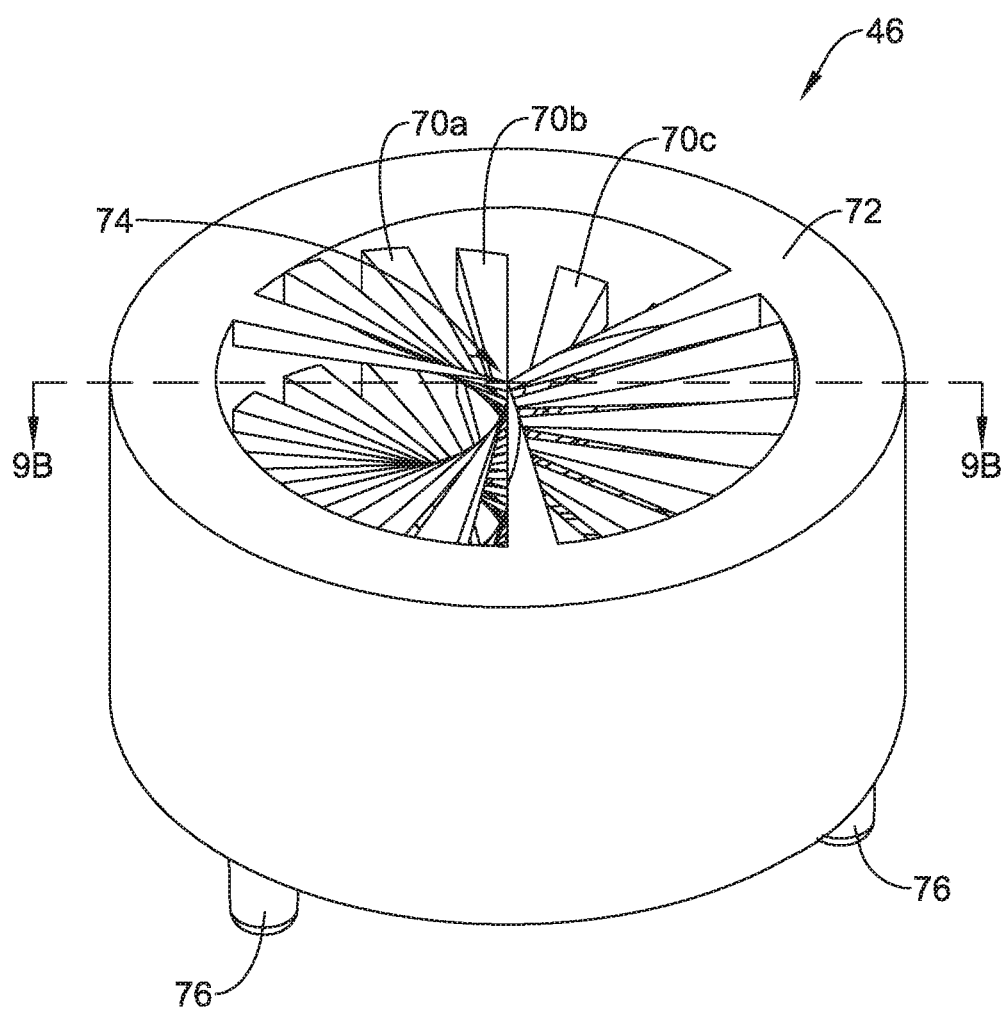
FIG. 9A is a perspective view of a brush section forming a portion of the biopsy cap of FIG. 1.
Figure 9B:
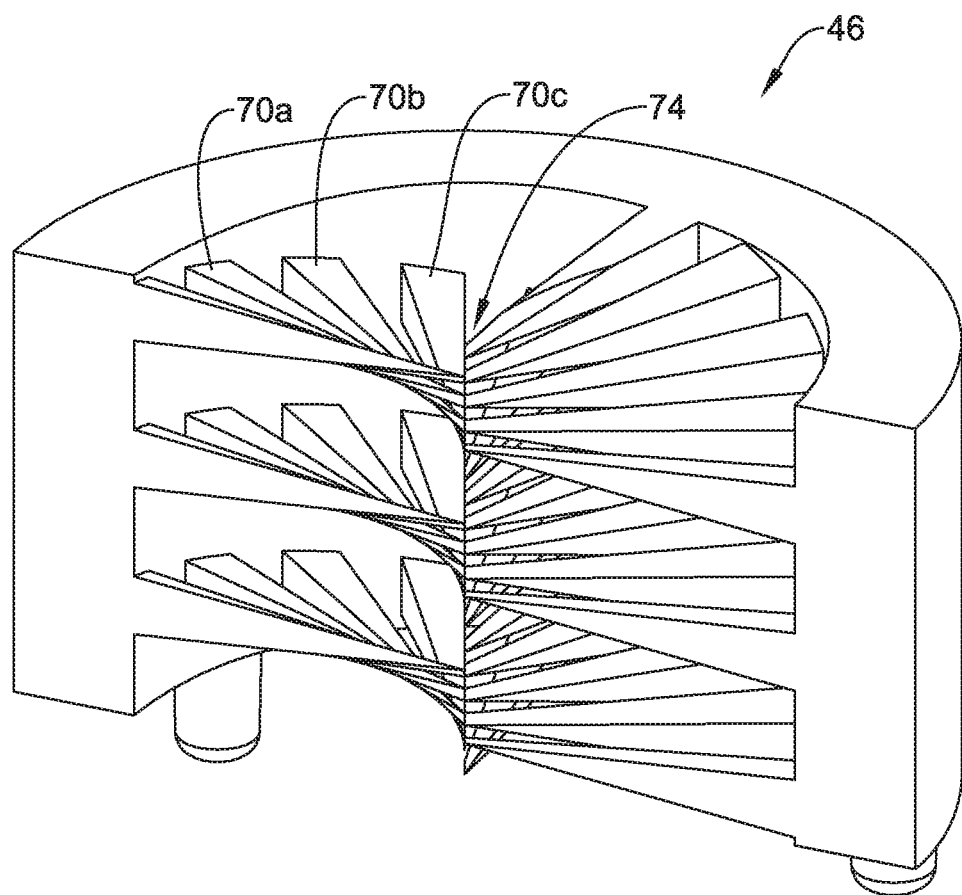
FIG. 9B is a perspective cross-sectional view of the brush section of FIG. 9A, taken along the line 9-9.

FIG. 9A is a perspective view of the brush section 46 while FIG. 9B is a cross-sectional view, taken along the line 9-9, of the brush section 46. As can be seen, the brush section 46 includes a plurality of individual brushes, such as a brush 70a, a brush 70b and a brush 70c. While there are a plurality of individual brushes, for clarity only a few are referenced. It can be seen that that each of the individual brushes 70a, 70b, 70c extend radially inwardly from an annular ring 72. In some cases, the individual brushes 70a, 70b, 70c may terminate at a terminal end proximate a center point 74 of the brush section 46. This center point 74 may correspond to where an elongate member extending through the biopsy cap 40 would extend through the brush section 46. The individual brushes 70a, 70b, 70c will deflect to enable the elongate member to extend through, but are biased into contact with the elongate member to help reduce or prevent fluid flow through the biopsy cap 40. In some cases, the brush section 46 may include alignment pins 76, which as will be discussed align with corresponding structures formed within the disk shutter section 44.

Figure 9C:
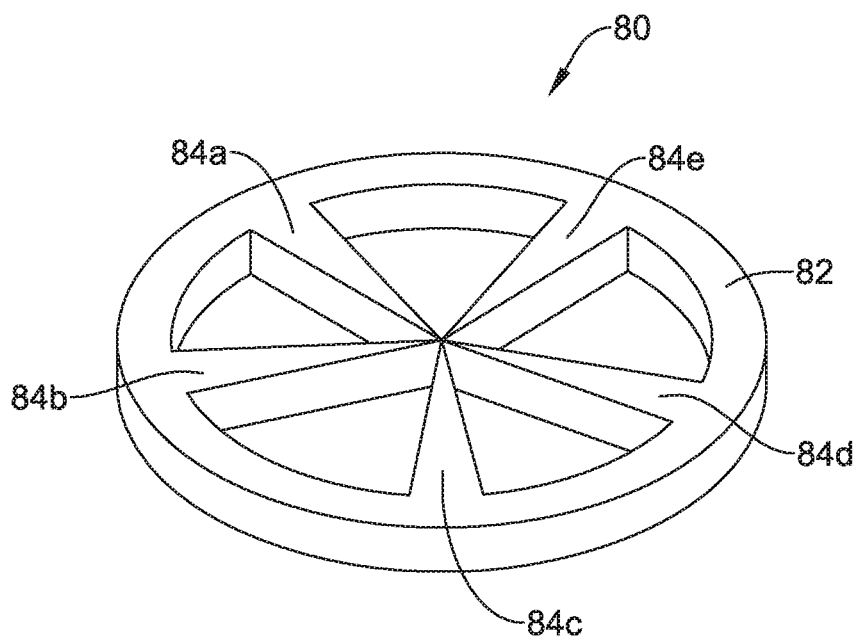
FIG. 9C is a perspective view of an individual brush layer forming a portion of the brush section of FIG. 9A.
Figure 9D:
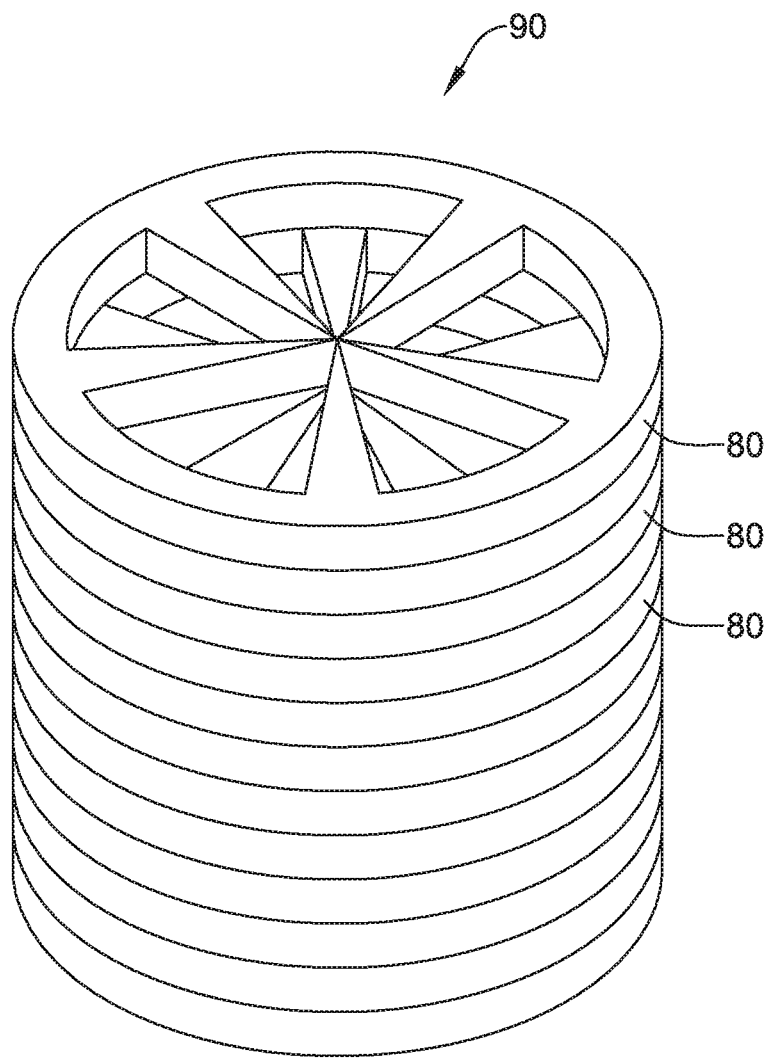
FIG. 9D is a perspective view showing a plurality of individual brush layers as shown in FIG. 9C compiled into an assembly in which each individual brush layer is rotated relative to adjacent individual brush layers.

In some cases, the brush section 46 may include a plurality of individual brush layers 80, as shown in FIG. 9C. The individual brush layer 80 includes an outer annular ring 82 and a total of five brushes 84a, 84b, 84c, 84d and 84e extending inwardly from the outer annular ring 82. While a total of 5 brushes are illustrated, it will be appreciated that this is merely illustrative, as the individual brush layer 80 may instead have two brushes, three brushes, four brushes, or even six or more brushes. FIG. 9D shows a brush section 90 that is formed by stacking together a plurality of individual brush layers 80. In forming the brush section 90, each individual brush layer 80 is rotated relative to the brush layer 80 adjacent that individual brush layer 80. As a result, the brushes are aligned in a helical fashion. In some cases, the brush section 90 may be considered as an example of the brush section 46.

Figure 9E:
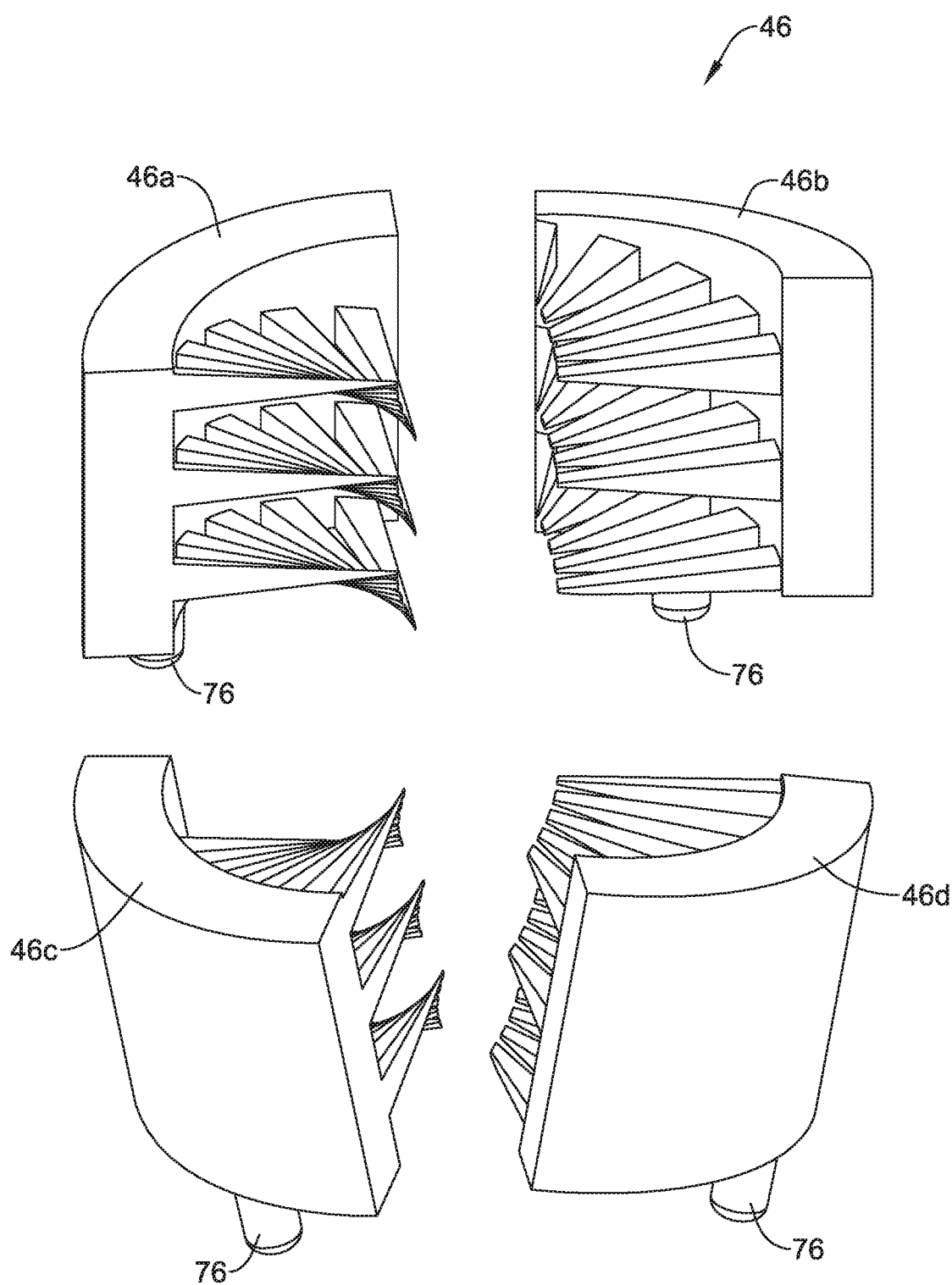
FIG. 9E is a perspective view of a brush section formed as a plurality of individual molded sections that may be combined together to form the brush section of FIG. 9A.

FIGS. 9A through 9D illustrate an example way of forming the brush section 46. FIG. 9E provides another way of forming the brush section 46. It can be appreciated that the brush section 46 may be a complicated structure to mold in its final configuration. In some cases, the brush section 46 may be molded as a plurality of individual sections that can then be adhesively secured together to form the brush section 46. As illustrated, FIG. 9E shows the brush section 46 divided into a total of four brush section portions labeled 46a, 46b, 46c and 46d. In other cases, the brush section 46 may be divided into two, three, five or more distinct section portions for molding.

Figure 9F:
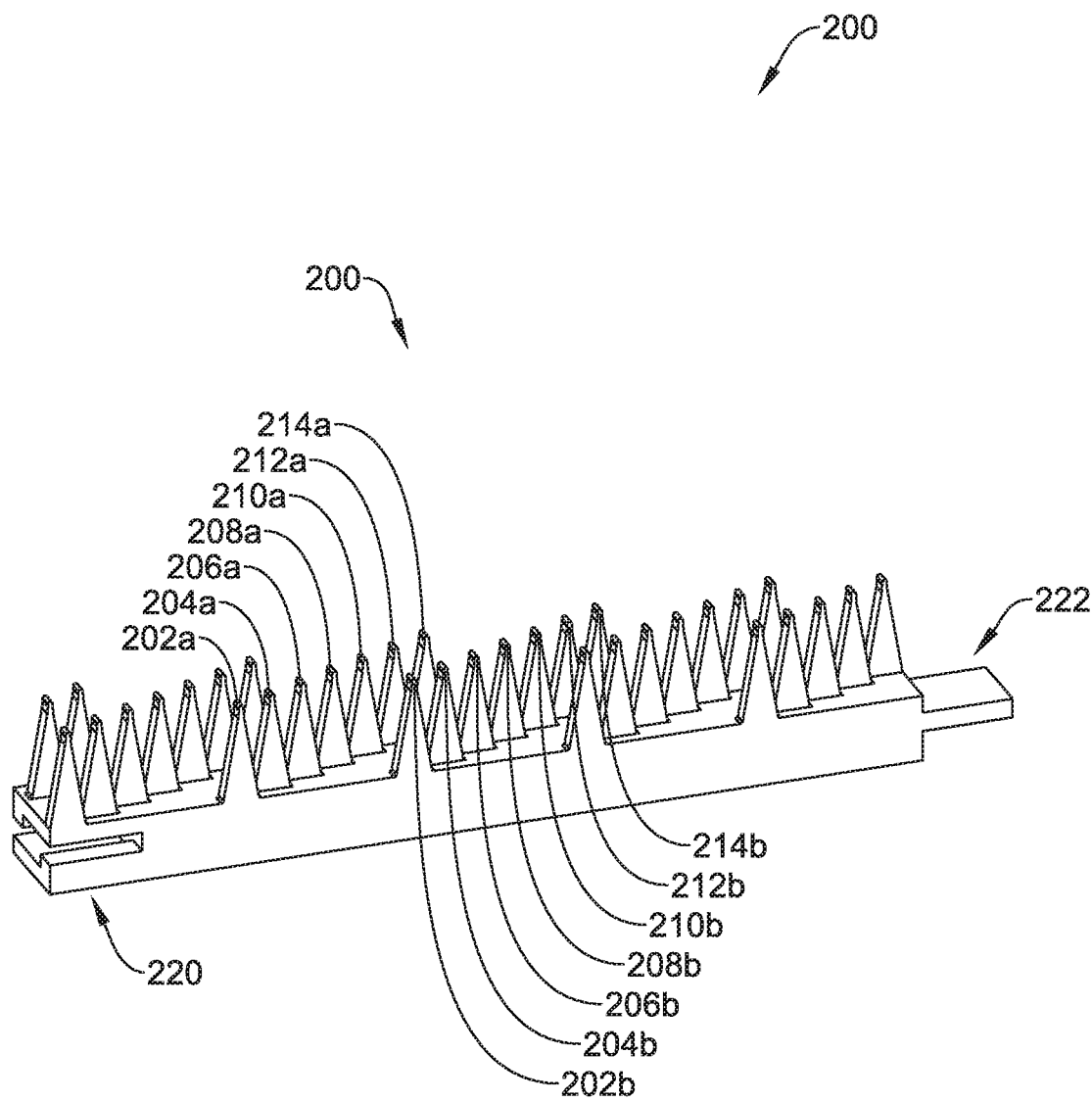
FIG. 9F is a perspective view of a linear molded structure that may be curved and secured together to form an example brush section usable in the biopsy cap of FIG. 1.
Figure 9G:
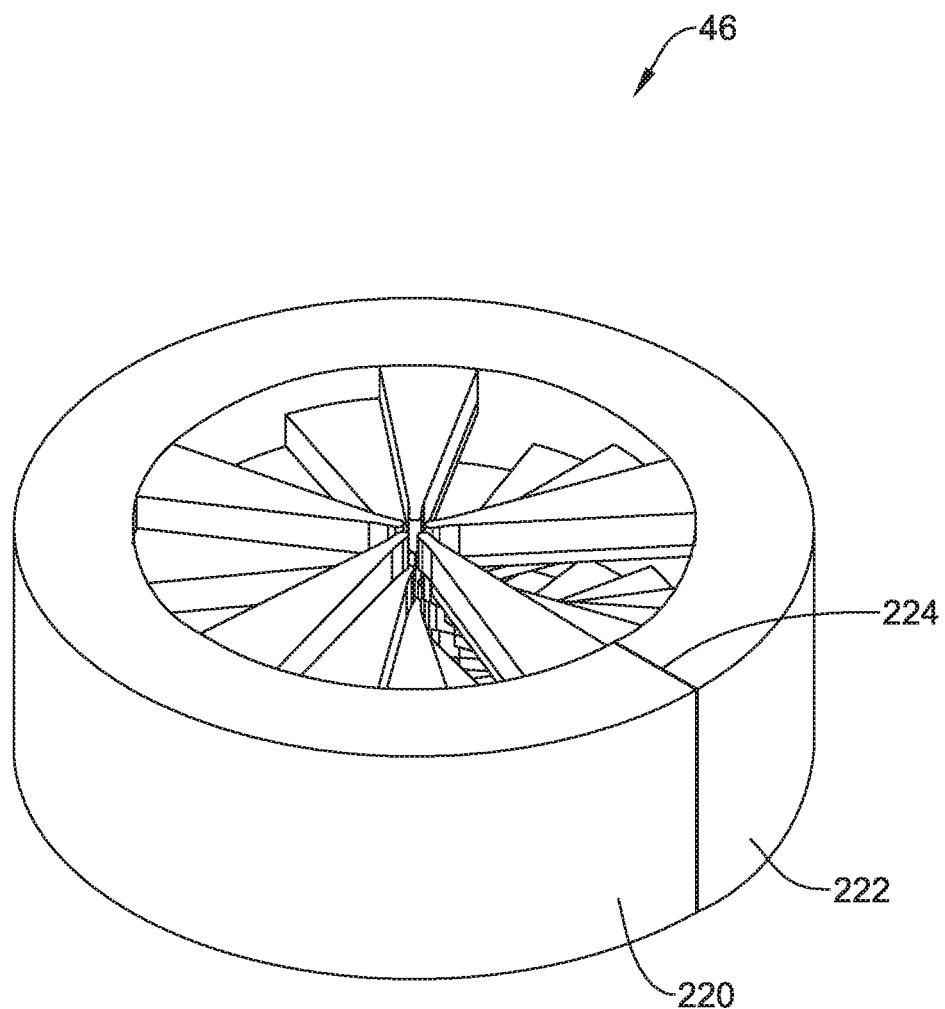
FIG. 9G is a perspective view of the linear molded structure of FIG. 9F, formed into a brush section.

FIG. 9F shows another example way of forming the brush section 46. In some cases, the brush section 46 may be formed by molding a linear molded structure 200 as shown in FIG. 9F. In some cases, the linear molded structure 200 may be formed by liquid silicone rubber injection molding, wire EDM cutting or compression molding. The linear molded structure 200 includes a section of bristles 202a, 204a, 206a, 208a, 210a, 212a, 214a, a section of bristles 202b, 204b, 206b, 208b, 210b, 212b, 214b and so on. In some cases, the linear molded structure 200, which may be formed for example out of silicone, may have a first free end 220 and a second free end 222. In some cases, the first free end 220 may be configured to fit into the second free end 222. The particular shape or configuration of the first free end 220 and the second free end 222 may take any of a variety of forms, as long as the shape of the first free end 220 is able to engage the second free end 222. Once the first free end 220 has been secured into the second free end 222, the resulting brush section 46 may be formed, as shown in FIG. 9G. It can be seen that the first free end 220 and the second free end 222 together form a joint 224.

Figure 9H:
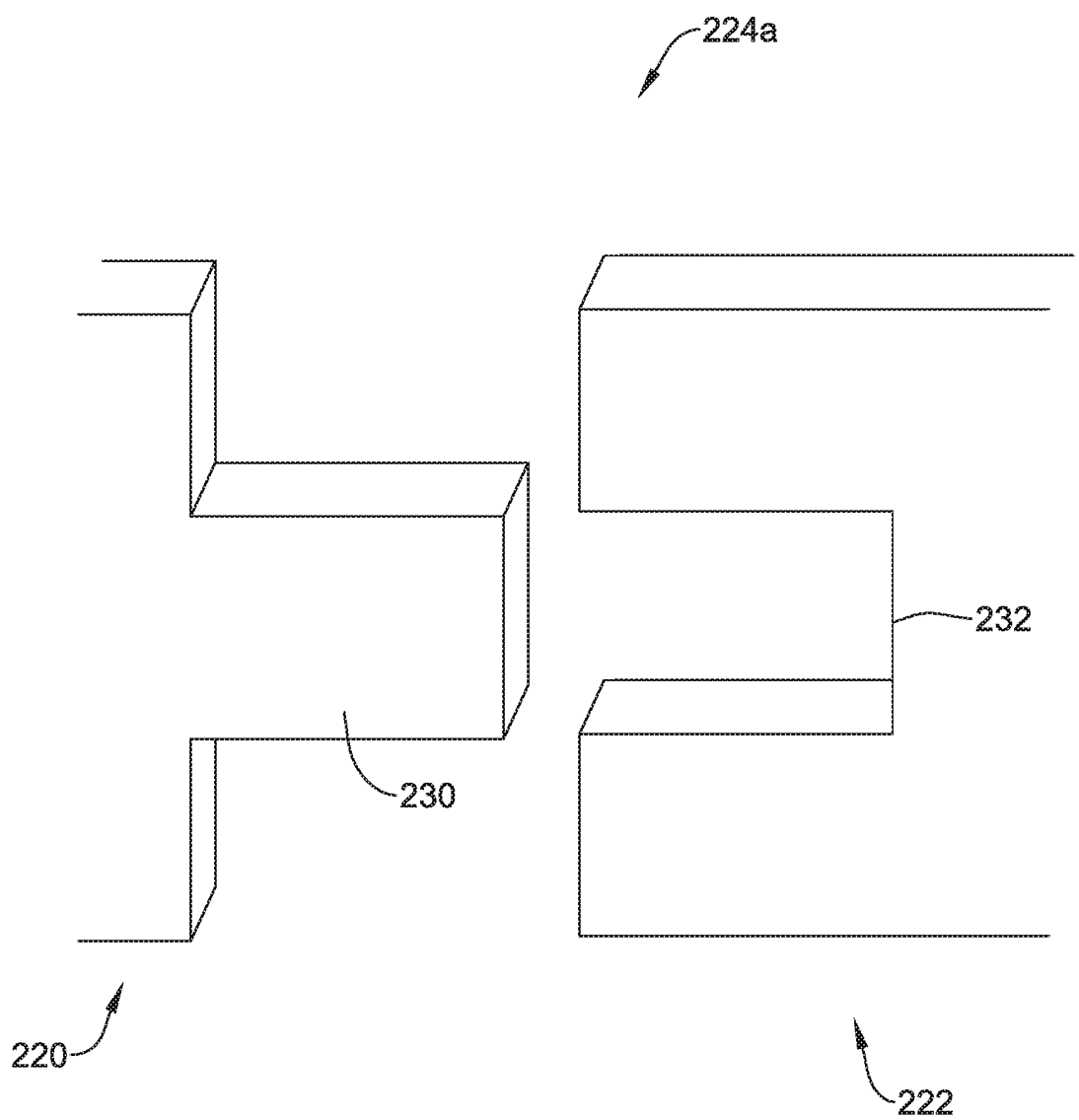
FIGS. 9H through 9J are views of illustrative joining techniques for securing together the free ends of the linear molded structure of FIG. 9F to form the brush section of FIG. 9G.
Figure 9I:
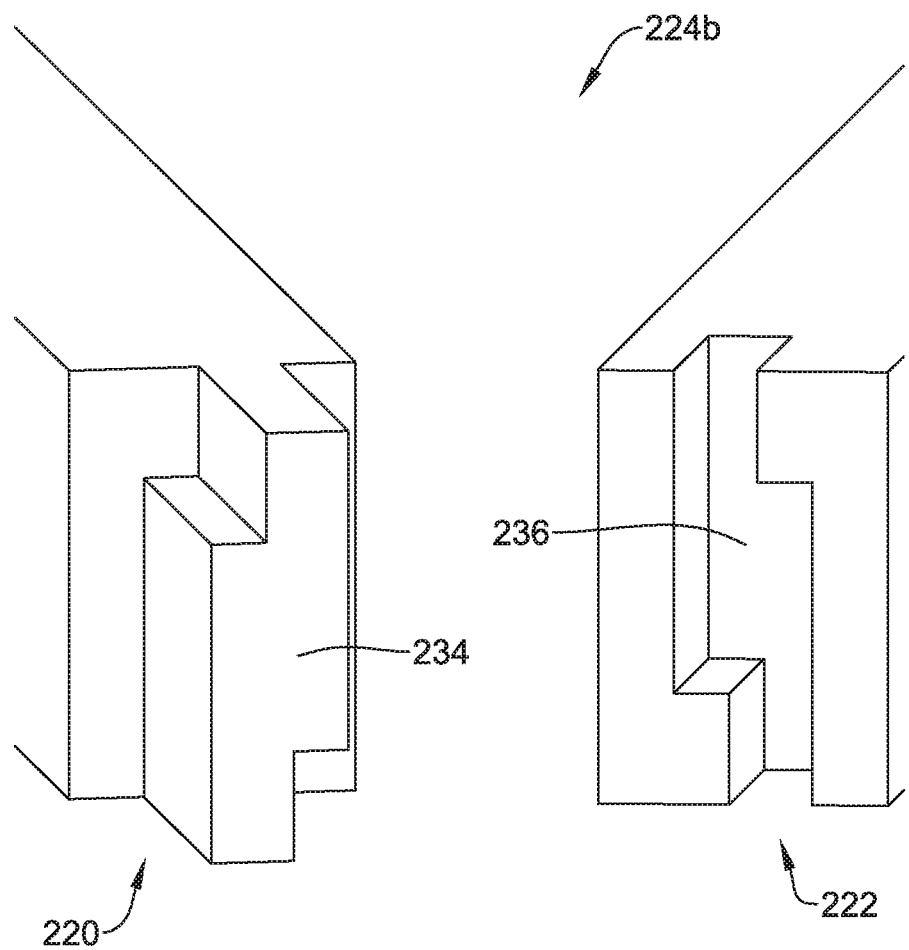
Figure 9J:
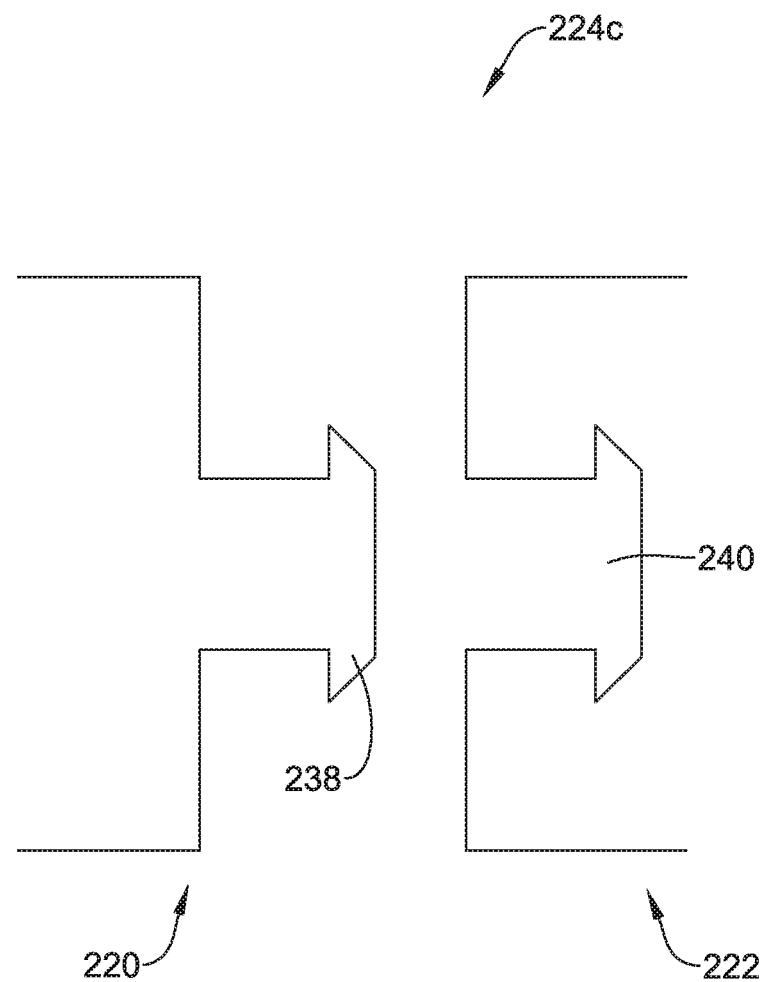

FIGS. 9H, 9I and 9J provide illustrative but non-limiting examples of how the first free end 220 and the second free end 222 may be configured to form the joint 224. FIG. 9H shows an interference fit, in which the first free end 220 includes a rectilinear tab 230 that is configured to form an interference fit within a rectilinear void 232 formed within the second free end 222 to form a joint 224a. In some cases, there may be sufficient friction between the tab 230 and the void 232 to hold the joint 224 together. In some instances, an adhesive may be added. FIG. 9I shows a joint 224b in which the first free end 220 includes a multi profile tab 234 that is configured to fit into a corresponding multi profile void 236 formed within the second free end 222. In some cases, there may be sufficient friction between the multi profile tab 234 and the multi profile void 236 to hold the joint 224b together. In some instances, an adhesive may be added. FIG. 9J shows a joint 224c that may be considered as being a buckle joint. The first free end 220 includes an arrow shaped tab 238 that is configured to fit into a corresponding arrow shaped void 240. In some cases, there may be sufficient friction between the arrow shaped tab 238 and the arrow shaped void 240 to hold the joint 224c together. In some instances, an adhesive may be added. It will be appreciated that these illustrated shapes are not intended to be limiting in any fashion.

Figure 9K:
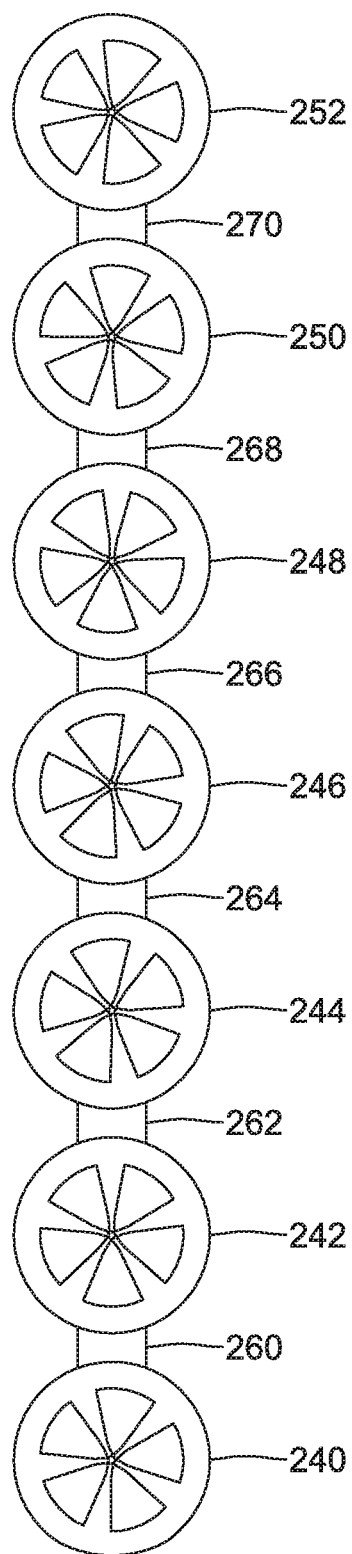
FIGS. 9K through 9T are views of brush layers that are secured to each other and folded together to form an example brush section.
Figure 9L:
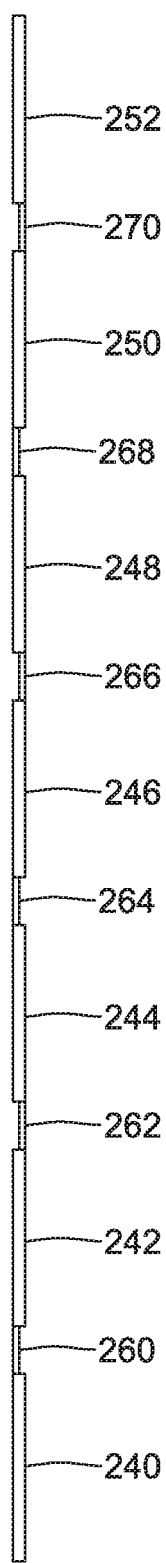
Figure 9M:
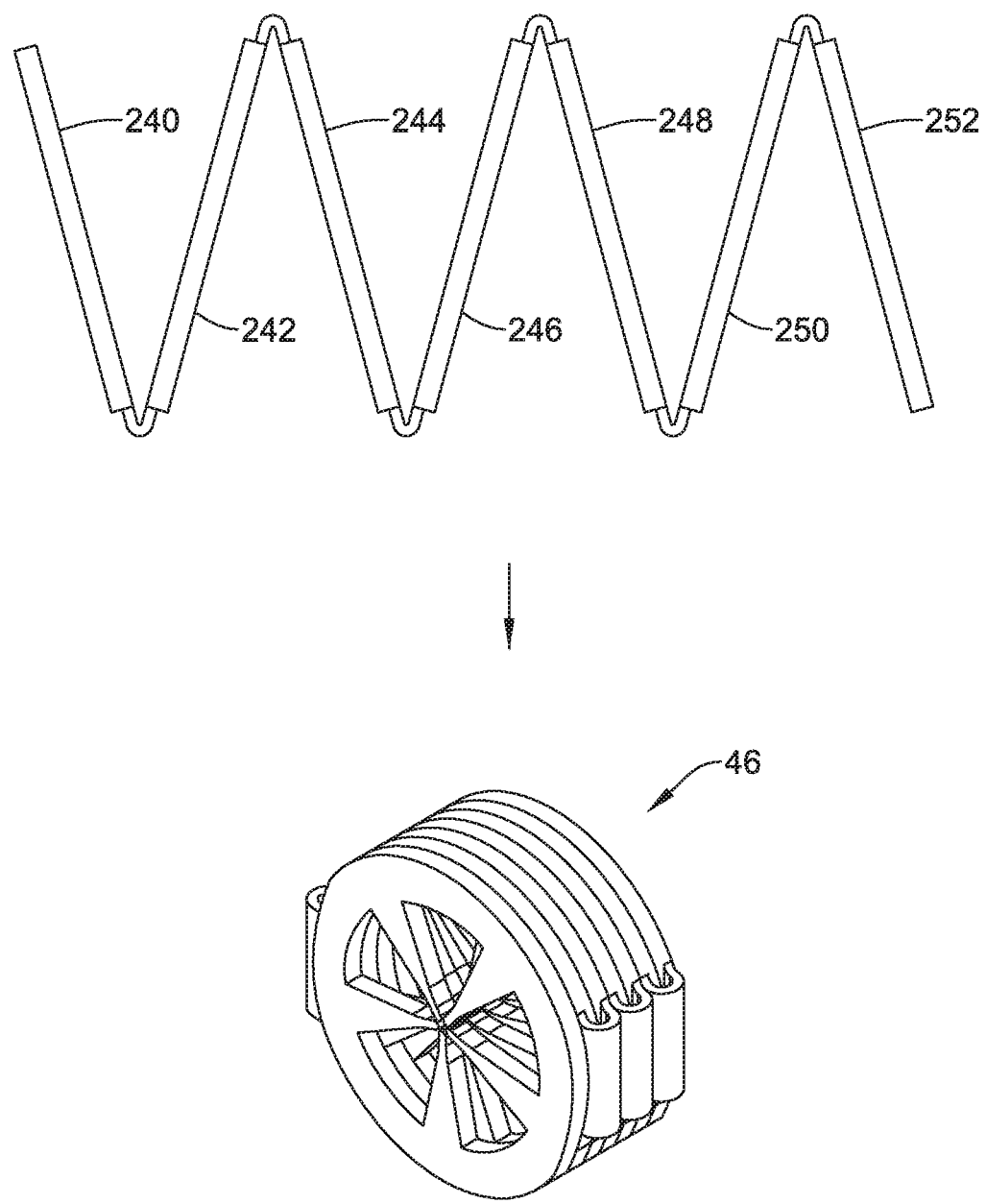

Another method of forming the brush section 46 includes molding or otherwise forming a plurality of brush layers that are secured together, and then folding the brush layers together. FIGS. 9K through 9N show an illustrative way of forming the brush section. FIG. 9K is a top view of a plurality of brush layers 240, 242, 244, 246, 248, 250 and 252 that are joined together via hinges 260, 262, 264, 266, 268, 270 and 272 while FIG. 9L is a side view thereof. As can be seen particularly in FIG. 9L, some of the hinges 260, 262, 264, 266, 268, 270 and 272 include a downward facing notch while others include an upward facing notch. A downward facing notch, such as shown as part of the hinges 260, 264 and 268 facilitate folding in a downward direction while up upward facing notch, shown as shown as part of the hinges 262, 266 and 270, facilitate folding in an upward direction. In some cases, the hinges 260, 262, 264, 266, 268, 270 and 272 may not include downward and upward facing notches, but may instead just include a thinned portion that facilitates folding. FIG. 9M shows how each of the brush layers 240, 242, 244, 246, 248, 250 and 252 may be folded in accordion fashion to form the brush section 46.

Figure 9N:
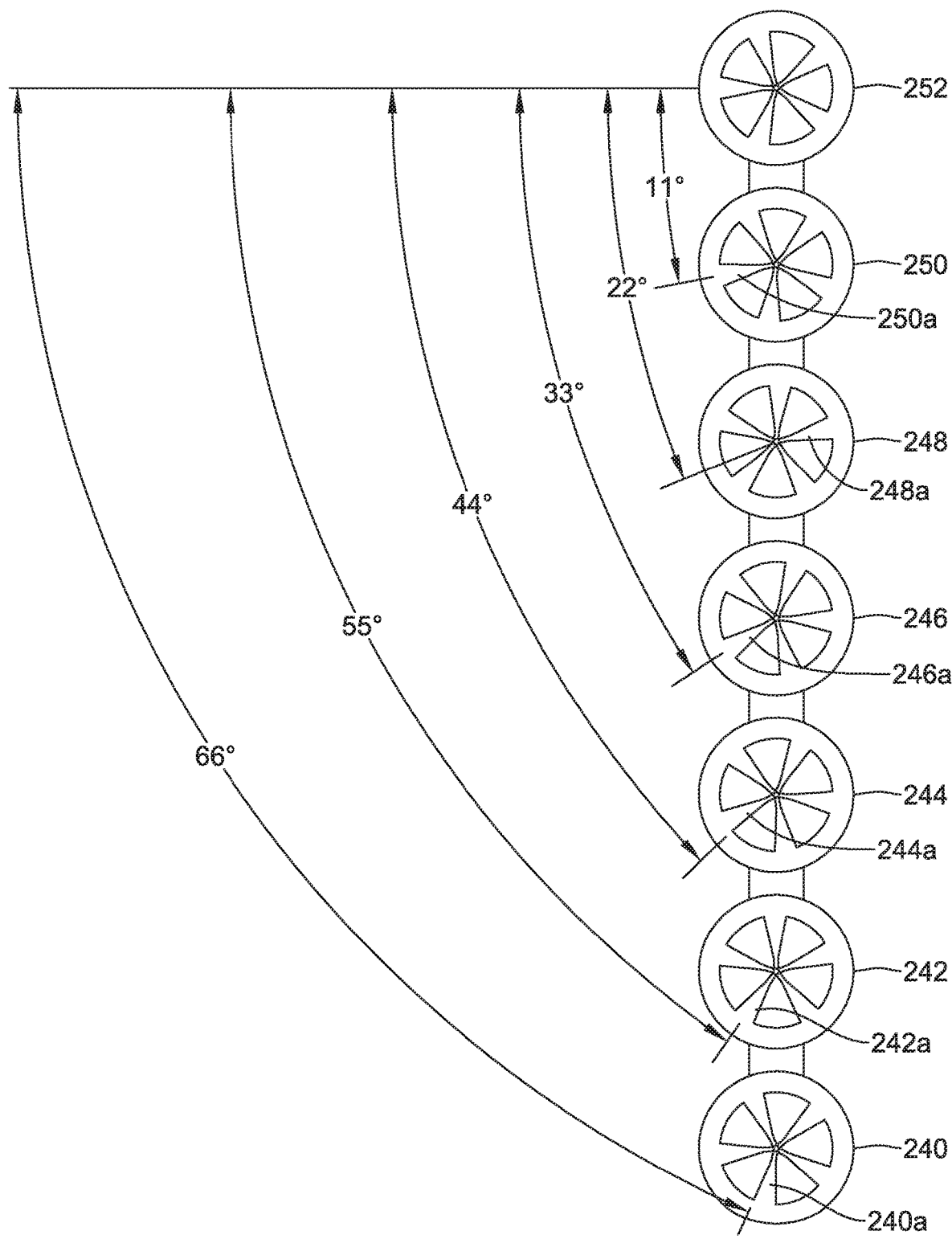

FIG. 9N is a graphical representation of how the individual bristles forming each of the brush layers 240, 242, 244, 246, 248, 250 and 252 may be rotated relative to each other. In some cases, as shown, each brush layer 240, 242, 244, 246, 248, 250 and 252 is rotated 11 degrees relative to each adjacent brush layer 240, 242, 244, 246, 248, 250 and 252. To illustrate, starting with a highlighted bristle 252a, a highlighted bristle 250a is rotated 11 degrees relative to the highlighted bristle 252a. A highlighted bristle 248a is rotated 22 degrees relative to the highlighted bristle 252a. A highlighted bristle 248a is rotated 22 degrees relative to the highlighted bristle 252a. A highlighted bristle 246a is rotated 33 degrees relative to the highlighted bristle 252a. A highlighted bristle 244a is rotated 44 degrees relative to the highlighted bristle 252a. A highlighted bristle 242a is rotated 55 degrees relative to the highlighted bristle 252a. A highlighted bristle 240 is rotated 66 degrees relative to the highlighted bristle 252a.

Figure 9O:
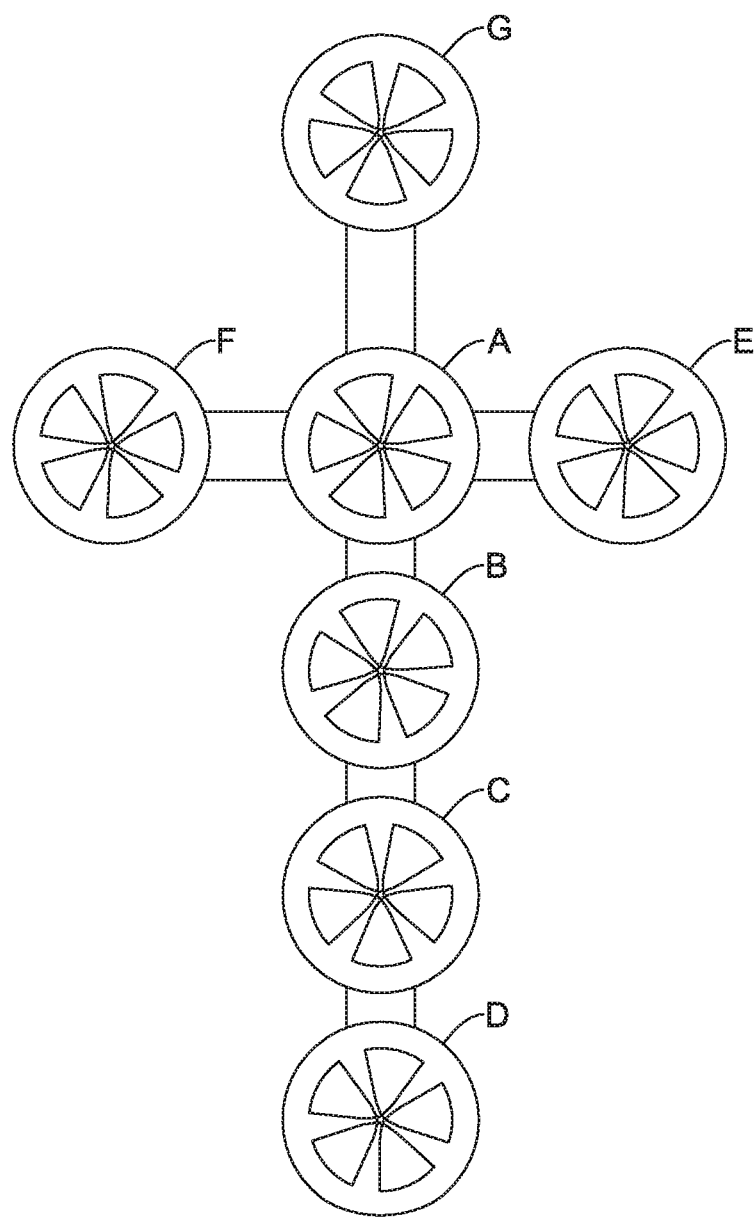
Figure 9P:
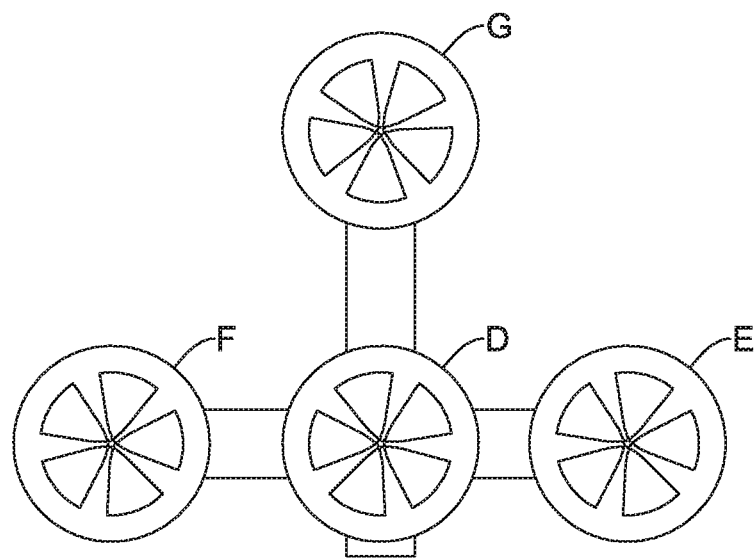
Figure 9Q:
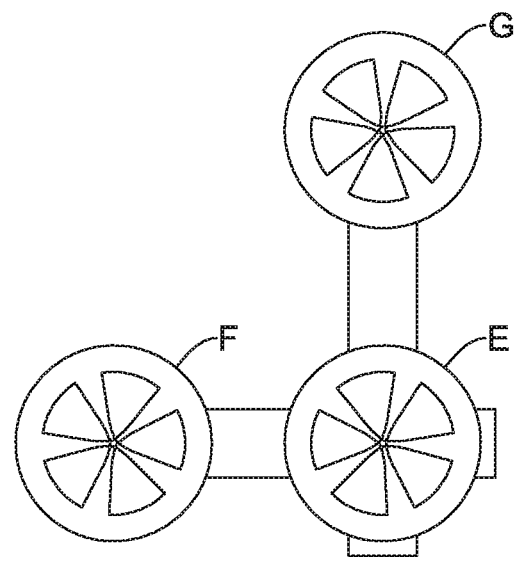
Figure 9R:
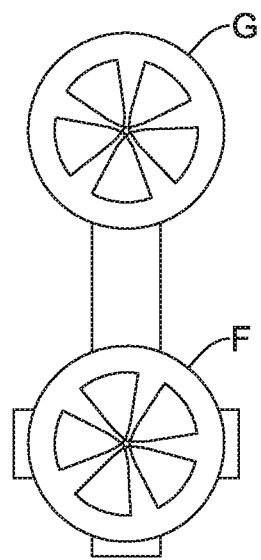
Figure 9S:
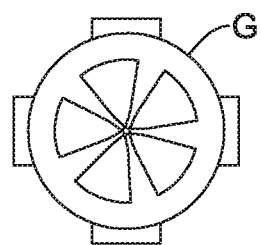
Figure 9T:
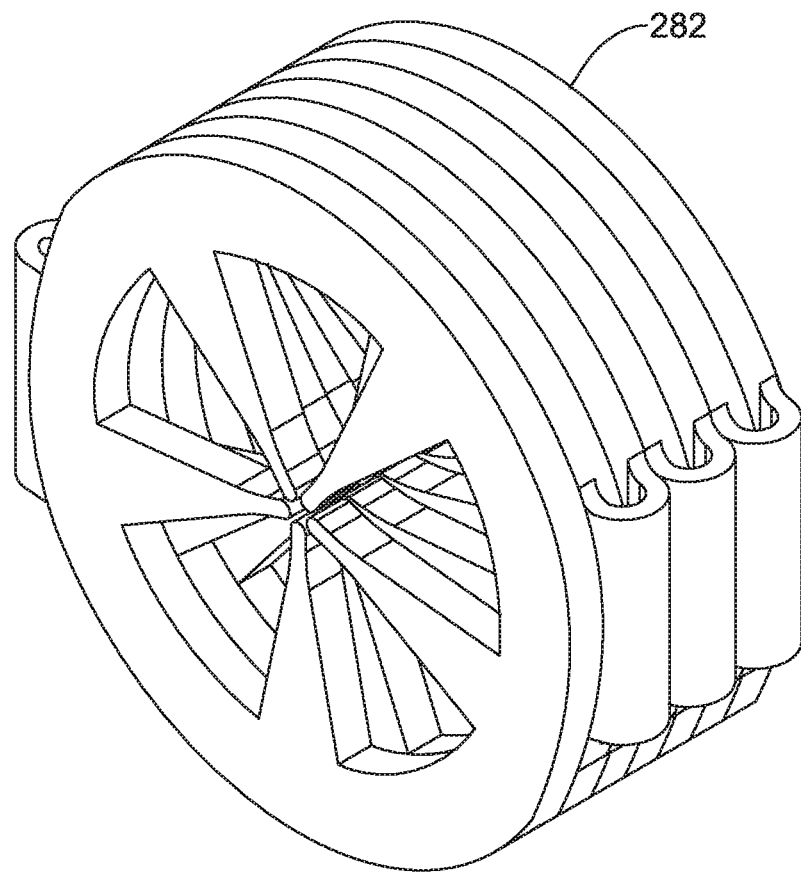

FIGS. 9O through 9T illustrate another way of folding together connected brush sections to form the brush section 46. A plurality of brush layers A, B, C, D, E and F are arranged and secured together in a 2 dimensional arrangement as shown in FIG. 9O. In a first step, as shown in FIG. 9P, brush layer B, brush layer C and brush layer D can be folded together in a zig-zag manner and folded over the brush layer A, resulting in the brush layer D being on the top of the stack after step 1. In step 2, shown in FIG. 9Q, the brush layer E is folded over the brush layer D, such that the brush layer E is on top of the stack after step 2. In step 3, shown in FIG. 9R, the brush layer F is folded over the brush layer E such that the brush layer F is on top of the stack after step 3. In step 4, shown in FIG. 9S, the brush layer G is folded over the brush layer F such that the brush layer G is on top of the stack after step 4. FIG. 9T shows a resulting brush stack 282, which may be used as the brush section 46.

Figure 10A:
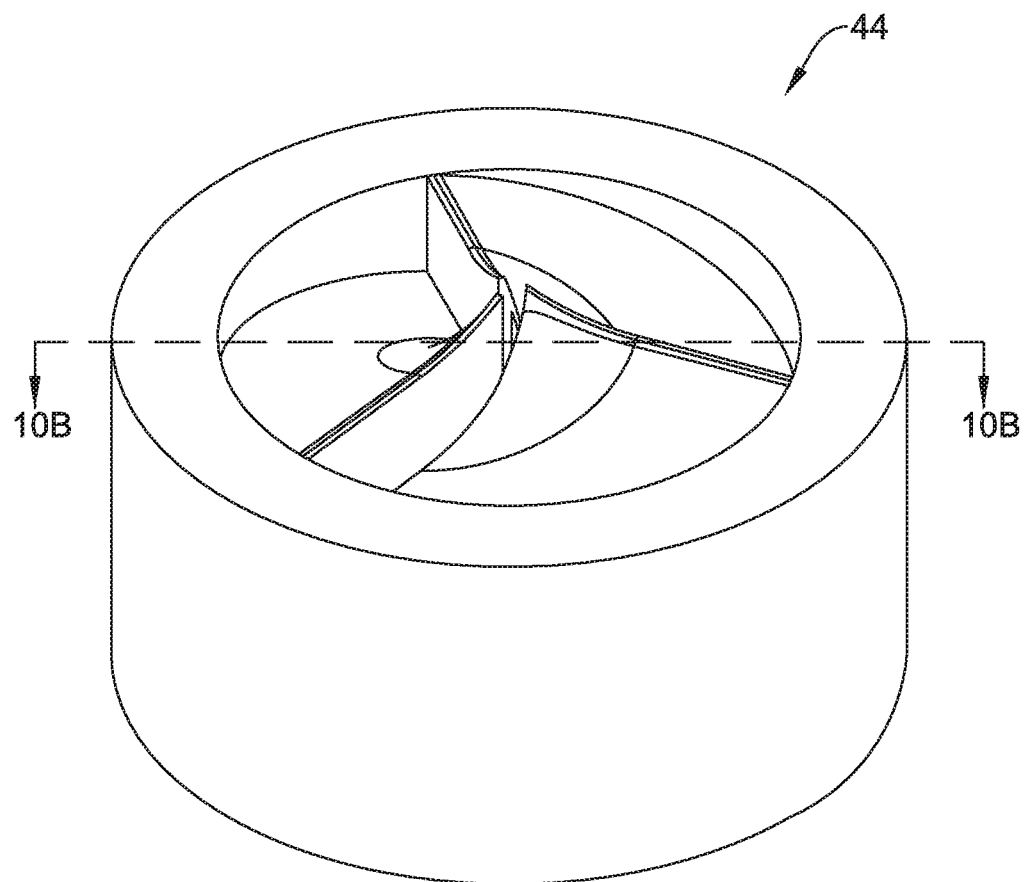
FIG. 10A is a perspective view of a disk shutter section forming a portion of the biopsy cap of FIG. 1.
Figure 10B:
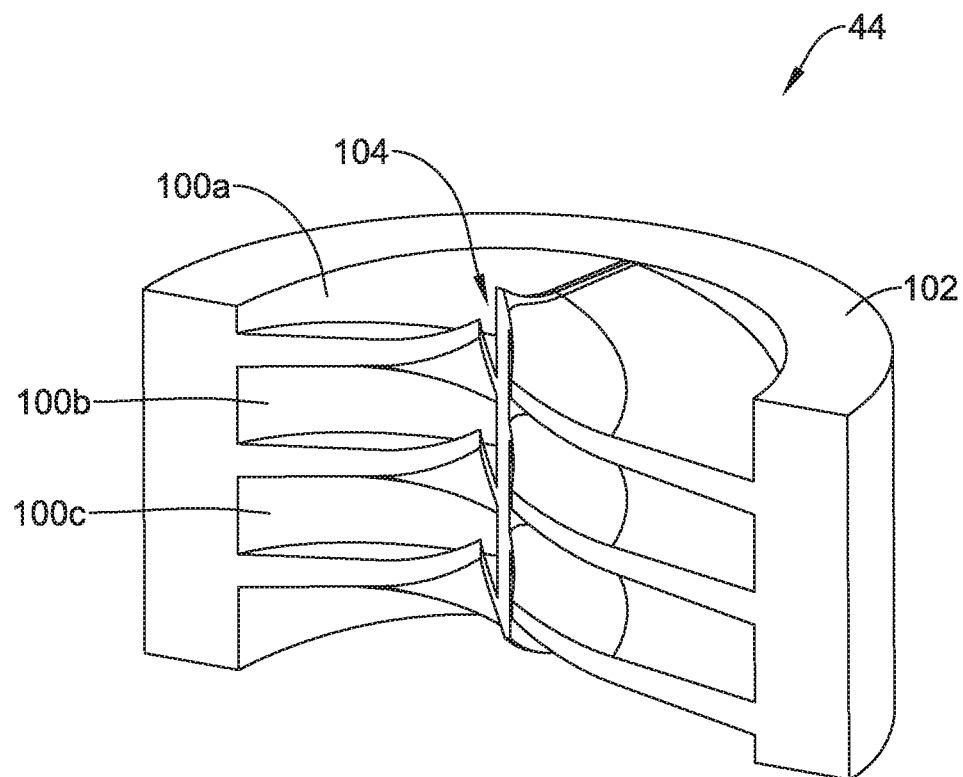
FIG. 10B is a perspective cross-sectional view of the disk shutter section of FIG. 10A, taken along the line 10-10.
Figure 10C:
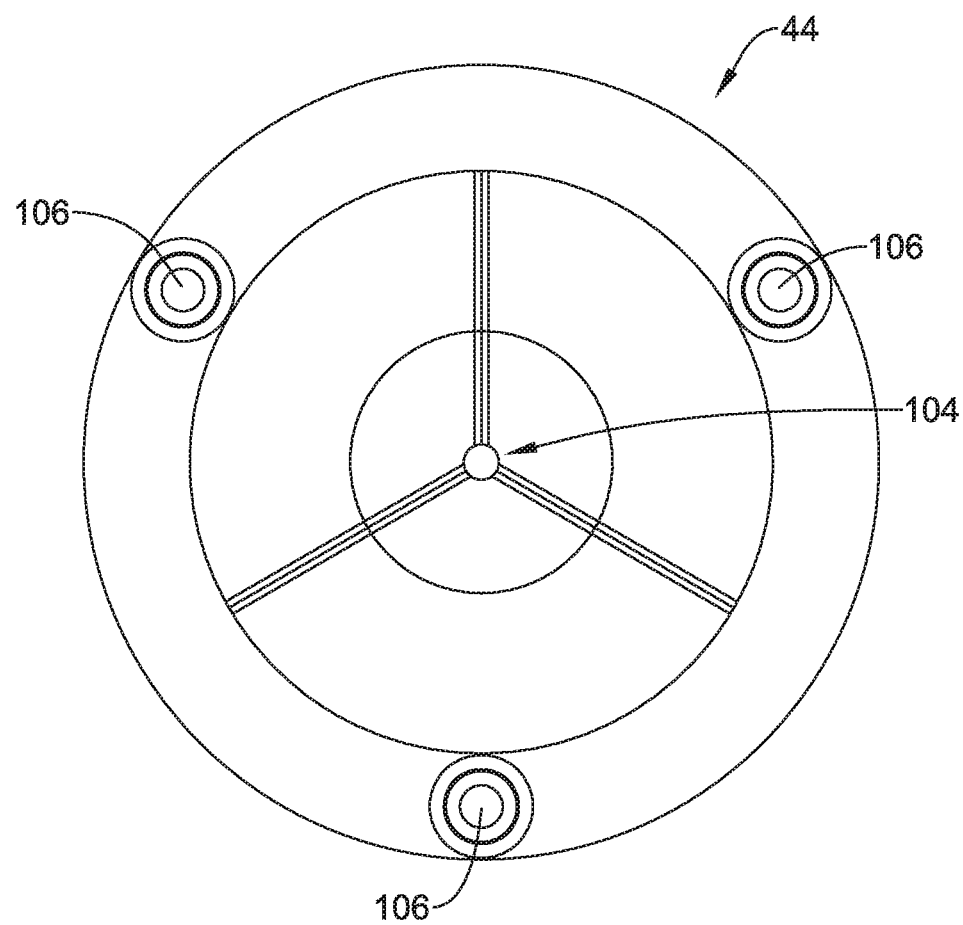
FIG. 10C is a bottom view of the disk shutter section of FIG. 10A.

FIG. 10A is a perspective view of the disk shutter section 44 while FIG. 10B is a cross-sectional view, taken along the line 10-10, of the disk shutter section 44. As can be seen, the disk shutter section 44 includes a plurality of fins 100a, 100b, 100c. While there are a plurality of fins, for clarity only several are labeled. As can be seen, the fins 100a, 100b, 100c extend inwardly from an annular ring 102 and terminate proximate a center point 104. As an elongate member is extended through the biopsy cap 40, the elongate member may pass through the disk shutter section 44 proximate the center point 104. It will be appreciated that an aperture formed proximate the center point 104 will be filled by the elongate member extending therethrough, and thus the elongate member will substantially fill and block the aperture, thereby preventing bile or other fluids from leaking through the disk shutter section 44. The fins 100a, 100b, 100c will deform to allow the elongate member to extend therethrough, but are biased into contact with the elongate member in order to block fluid flow through the biopsy cap 40. In some cases, one or more of the fins 100a, 100b, 100c will extend into any slot extending along the elongate member, also helping to prevent fluid flow therethrough. In some cases, if multiple elongate members extend through the biopsy cap 40, one or more of the fins 100a, 100b, 100c may extend into spaces between the elongate members, thereby helping to block flow past the elongate members. FIG. 10C is a bottom view of the disk shutter section 44, showing alignment features 106 that are complementary to the alignment pins 76 extending from the brush section 46.

Figure 11:
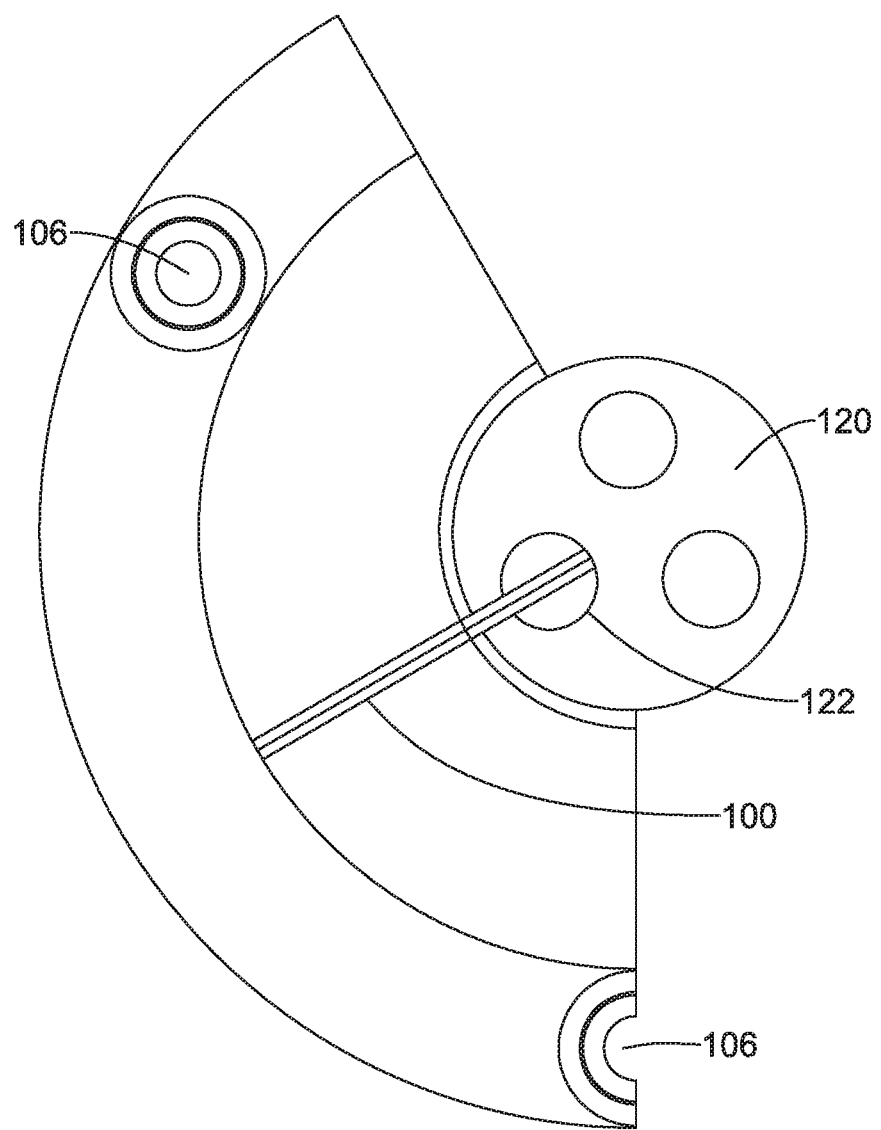
FIG. 11 is a perspective view showing a portion of the disk shutter section of FIG. 10A interacting with a C-shaped channel of a catheter extendable through the biopsy cap of FIG. 1.
Figure 12:
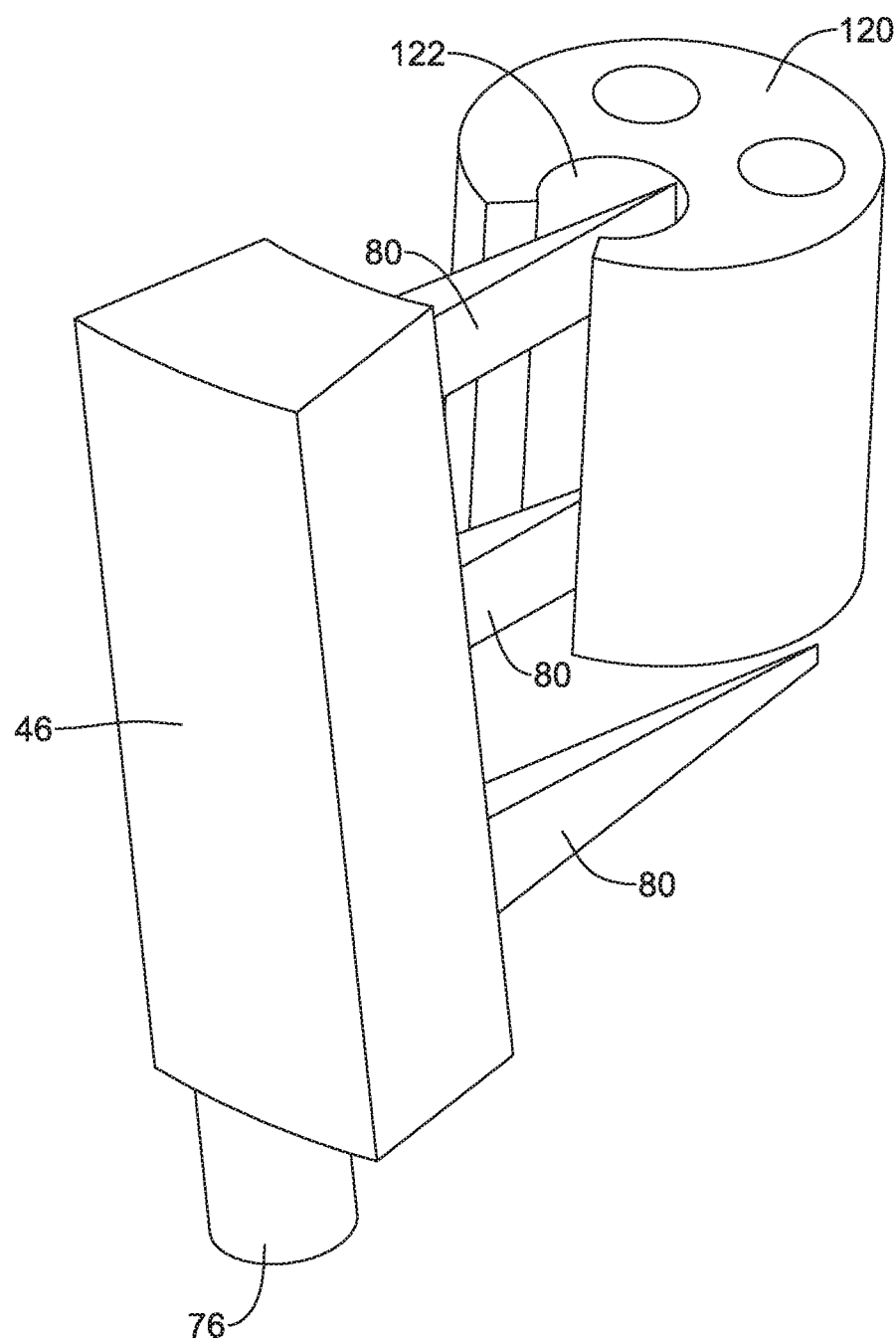
FIG. 12 is a perspective view showing a portion of the brush section of FIG. 9A interacting with a C-shaped channel of a catheter extendable through the biopsy cap of FIG. 1.

FIG. 11 shows a portion of the disk shutter section 44, shown from below, engaged with a catheter 120. The catheter 120, as shown, includes a C-shaped channel 122. As can be seen, one or more fins 100 extend into the C-shaped channel 122 and thus help to prevent fluid flow through the C-shaped channel 122 that could otherwise bypass other sealing mechanisms within the biopsy cap 40 and thus the fins help to prevent fluid flow through the biopsy cap 40. In some cases, the fins 100 may be arranged in a helical fashion to help accommodate twisting in the catheter 120, which could otherwise mis-align the C-shaped channel 122 with the fins 100. Similarly, FIG. 12 shows a portion of the brush section 46 with several brushes 80 engaged within the C-shaped channel 122. The brushes 80 are aligned in a helix format to accommodate twisting in the catheter 120.

In some cases, the relative dimensions of various portions of the biopsy cap 40 may be modified to accommodate the dimensions and profiles of whichever elongate members are to be extended through the biopsy cap 40. For example, the C-shaped channel 122 may have an opening width of 0.65 millimeters (mm). The disk shutter section 44 may have fins that are 0.2 mm in thickness. In some cases, the brush section 46 may have individual brushes 80 that have a distal end dimension (nearest the center point 74) that is 0.2 mm and a proximal end dimension (nearest the annular ring 76) that is 1.15 mm. In some cases, the brushes 80 are long enough to compress within the C-shaped channel 122, thereby helping to prevent fluid flow through the C-shaped channel 122. These dimensions are merely illustrative.

FIGS. 13A-18 illustrate example locking members that may be utilized with the biopsy caps disclosed herein. These locking members may be attached to a biopsy cap at any suitable position thereon and they may be used to secure the position of a medical device (e.g., a guidewire, catheter, etc.) relative to the cap (and/or the endoscope 10). Some of the additional cap structure is omitted from these Figures for simplicity purposes. However, it can be appreciated that any of the locking members shown and contemplated may be attached to a biopsy cap using conventional methods to achieve the desired result.

Figure 13A:
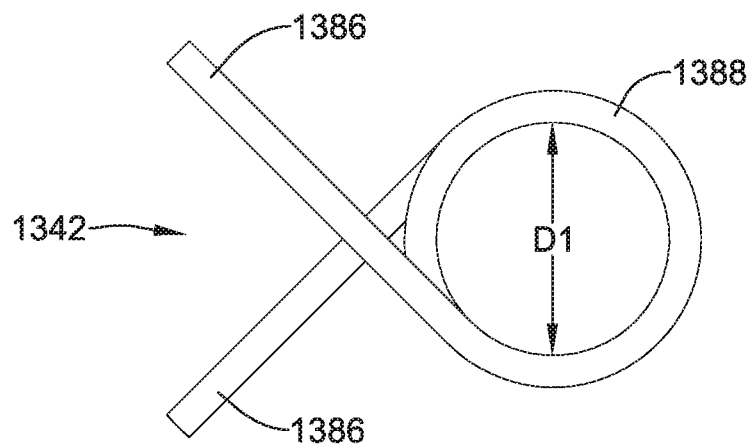
FIG. 13A is a perspective view of an example locking member in a first configuration.
Figure 13B:
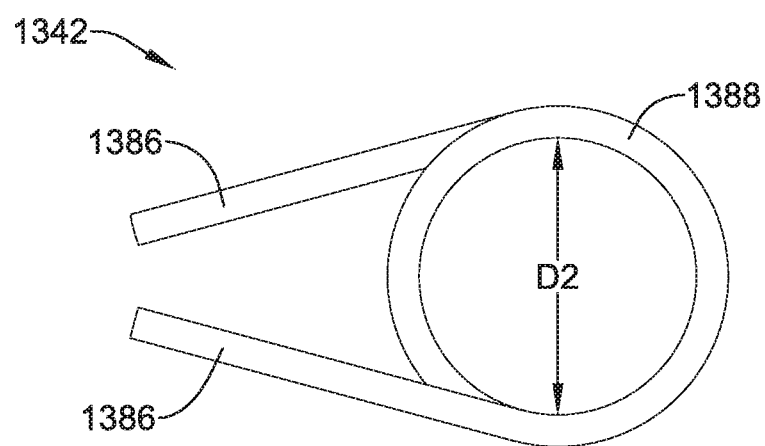
FIG. 13B is a perspective view of the example locking member illustrated in FIG. 13A in a second configuration.

FIGS. 13A and 13B illustrate locking member 1342, which may be configured to shift between a first configuration (as illustrated in FIG. 13A) and a second configuration (as illustrated in FIG. 13B). The locking member 1342 may include a pair of actuating arms 1386 that, when actuated, shift a locking ring 1388 from the first or smaller configuration that defines a smaller diameter D1 to the second or larger configuration that defines a larger diameter D2. The locking member 1342 may be described as being a spring clip or spring wing as the locking ring 1388 may include a plurality of loops of material with a spring-like configuration. The extra portion or loops of the "spring" may be utilized to accommodate the expansion in size of the ring 1388. In at least some embodiments, the locking member 1342 may have a form similar to a clip that may be used to secure weights onto a barbell.

Although not shown, locking member 1342 may be attached to a biopsy cap at any suitable location using any suitable means. For example, a portion of the arms 1386 and/or the ring 1388 may be directly attached to a cap. Alternatively, an arm or member may extend from the cap that attaches to the locking member 1342. In still other embodiments, the locking member 1342 may include an additional structure such as a clip to removably secure the locking member 1342 to a cap. These later embodiments of the locking member 1342 and other locking members may be desirable because they may allow different types of locking members to be "mixed and matched" based on their particular applicability to a given intervention. It can be appreciated that a number of securing members are also contemplated that take a form similar to the locking member 1342 and that are used to secure a cap to a port.

Figure 14:
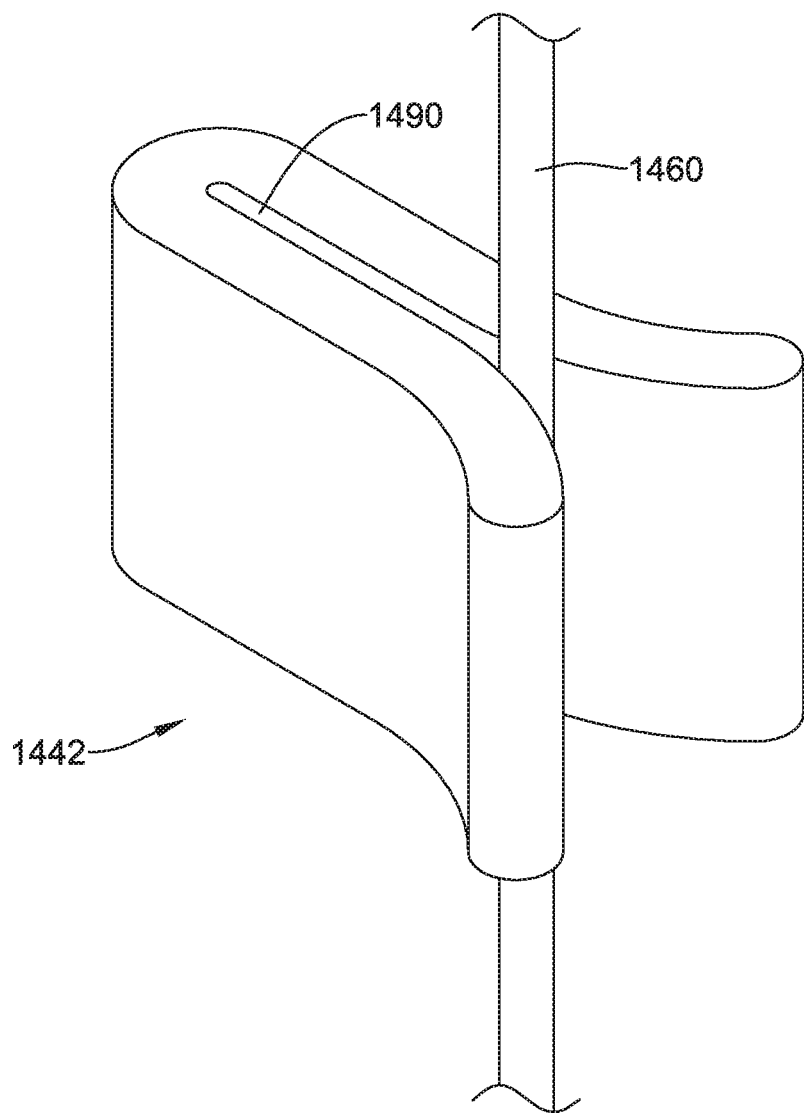
FIG. 14 is a perspective view of another example locking member.

FIG. 14 illustrates another example locking member 1442, which may be used with any of the biopsy caps disclosed herein. The locking member 1442 may have a wedge-like shape and may have a channel or groove 1490 formed therein where device 1460 (e.g., a guidewire, catheter, etc.) can be disposed therein and held by friction. Just like the other locking members disclosed herein, the locking member 1442 may be attached to a biopsy cap at any suitable location using any suitable means.

Figure 15A:
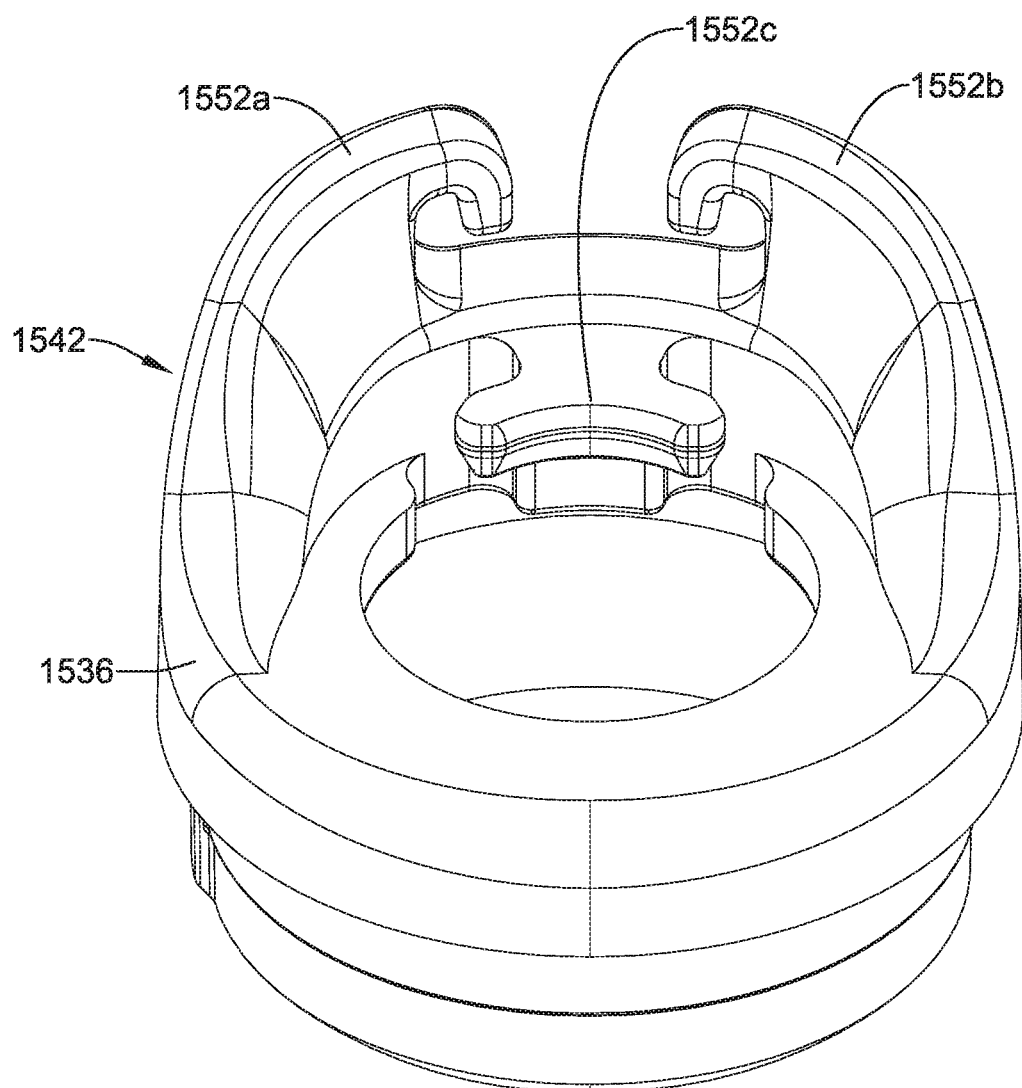
FIG. 15A is a perspective view of another example locking member.

FIG. 15A illustrates another example locking member or locking assembly 1542, which may be used with any of the biopsy caps disclosed herein. The locking member 1542 may include a plurality of locking features including, for example, a pair of arms 1552a/1552b that are coupled to or integrally formed on a shell 1536. The arms 1552a/1552b may be shaped in a manner that may allow them to secure the position of a device (e.g., a guidewire, catheter, etc.). For example, the arms 1552a/1552b may include one or more bends, hooks, grooves, and/or the like. The locking member 1542 may also include another locking structure or arm 1552c that may be disposed below the arms 1552a/1552b. By virtue of having this position, the arm 1552c may be used in conjunction with one or more of the arms 1552a/1552b to allow the device to be wrapped around the desired combination of the structures 1552a/1552b/1552c.

Figure 15B:
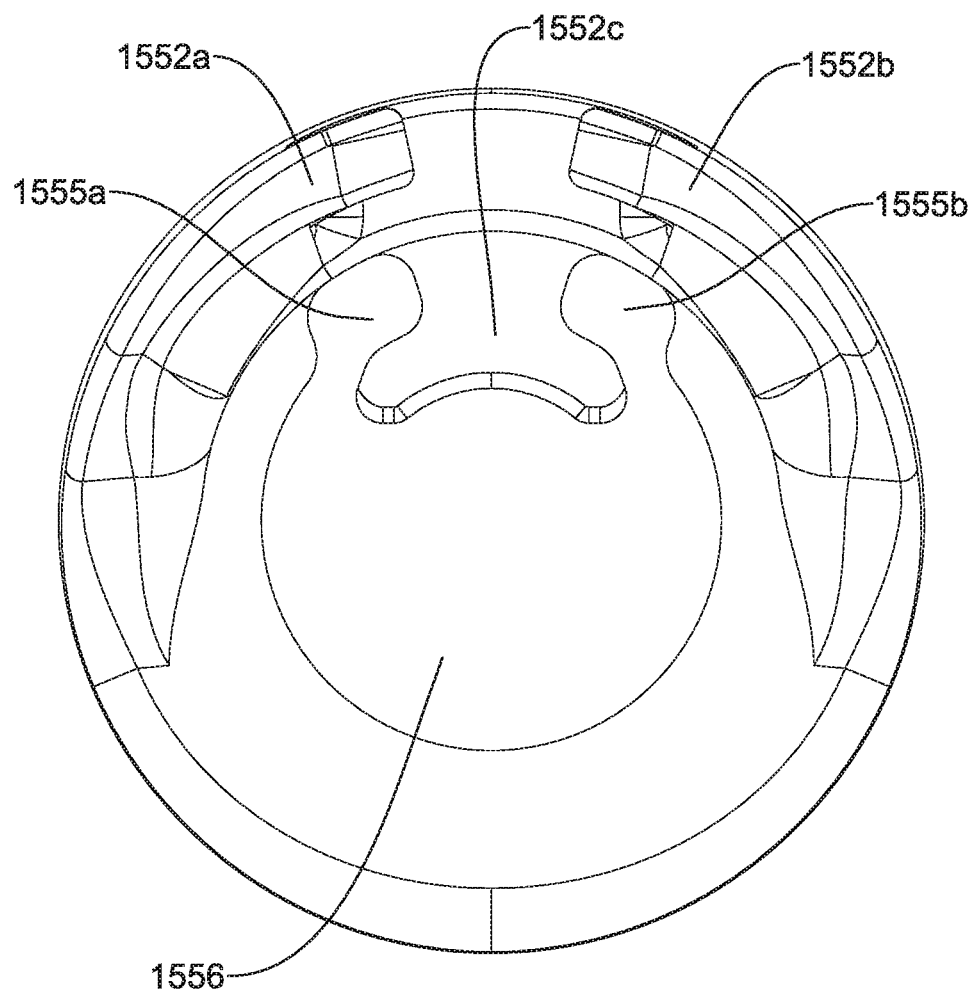
FIG. 15B is a perspective view of an alternative locking member to that depicted in FIG. 15A.

As illustrated in FIG. 15B, which is a rotated view of the locking member 1542 of FIG. 15A, the arm 1552c is shaped to create slotted openings 1555a/1555b in cooperation with the opening 1556 in the upper end of the shell. In some embodiments, the slotted opening is shaped with a narrowed opening which expands into a larger instrument holding area that has contoured surfaces for easy placement and removal of an instrument.

Figure 15C:
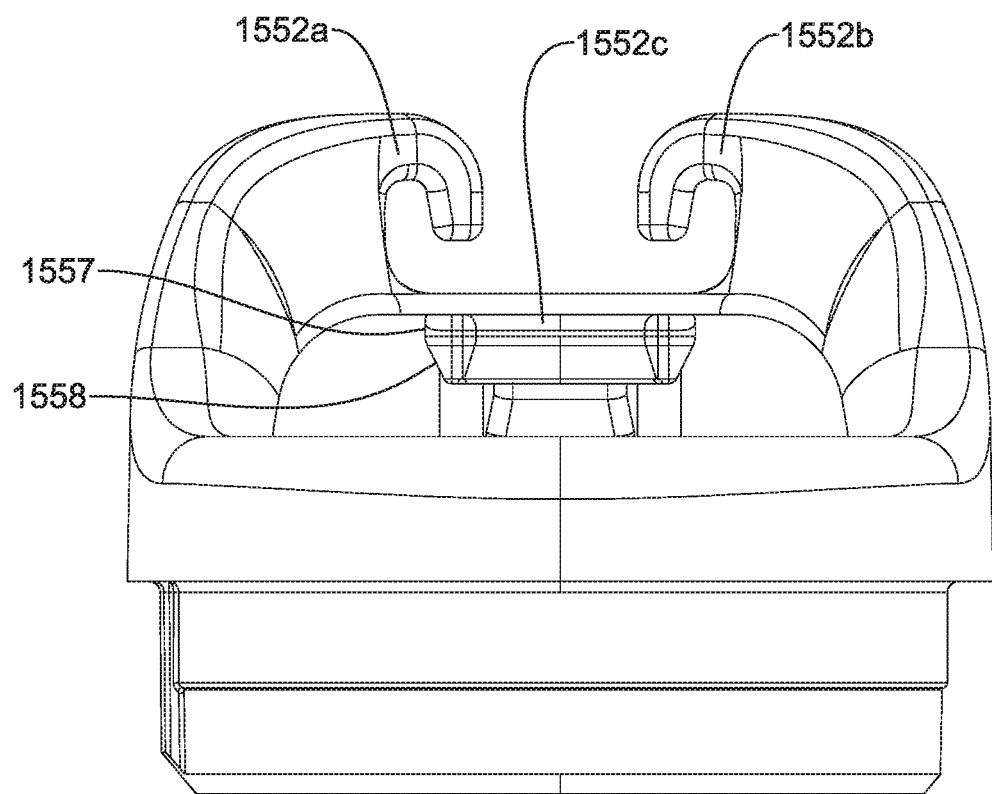
FIG. 15C is a perspective view of the alternative locking member of FIG. 15B showing further details.

FIG. 15C provides further detail of an exemplary design of arm 1552c. As indicated, the surface of the arm 1552c is contoured to provide easy movement of a guidewire or instrument around its surface. Further, the edge 1557 includes an open shoulder 1558 along the lower portion of the lateral surface of the arm 1552c. This surface helps prevent instruments from catching on the arm 1552c.

Figure 16:
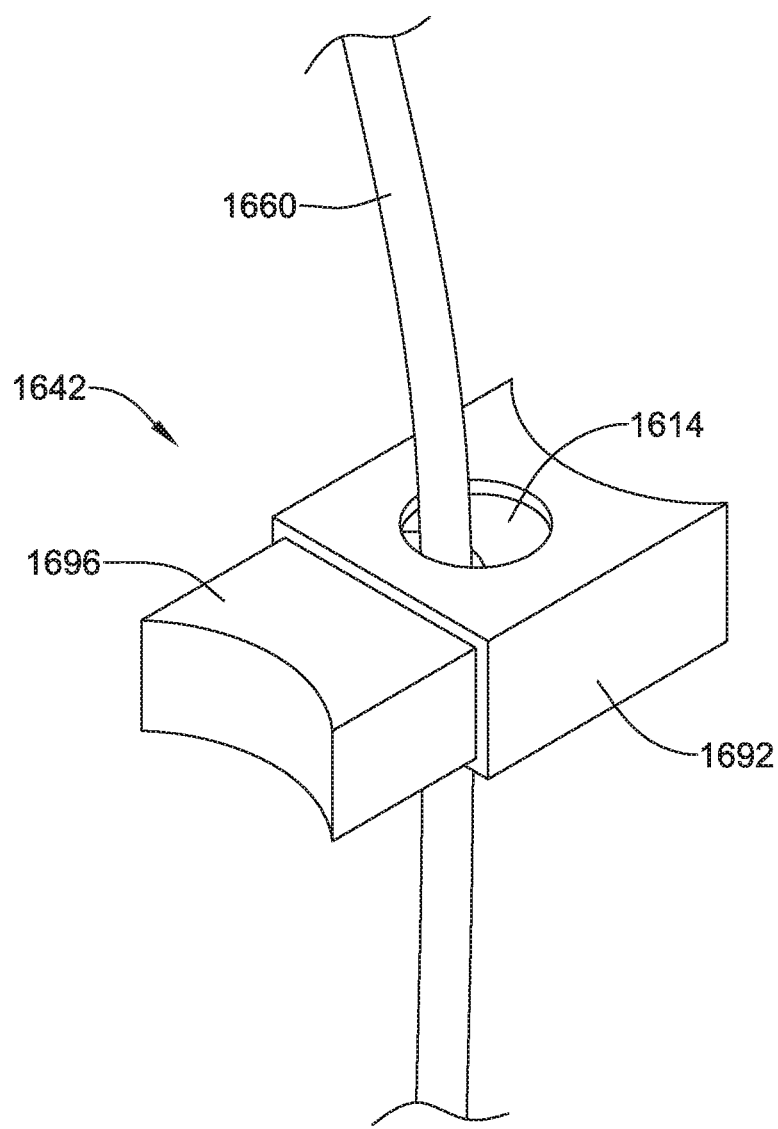
FIG. 16 is a perspective view of another example locking member.

FIG. 16 illustrates another example locking member 1642, which may be used with any of the biopsy caps disclosed herein. The locking member 1642 may include a base 1692 having an opening 1614 formed therein. A device 1660 may extend through the opening 1614. A spring button 1696 may be attached to the base 1692. The spring button 1696 may be coupled to a spring (not shown) that biases a portion of the button 1696 (e.g., a rear portion of button 1696 that may be disposed within the base 1692 on the opposite side of the opening 1614) into the opening 1614, thereby "closing" or "locking" the opening 1614. Depressing the button 1696 may overcome the bias and open the opening 1614 so that the device 1660 can be extended therethrough. Releasing the button 1696 allows the spring to press the button 1696 back into the biased position and lock the position of the device 1660.

A number of different configurations are contemplated for the locking member 1642. For example, the locking member 1642 may have a barrel-like or cylindrical shape rather than the more squared or rectangular shape as shown. In addition, the locking member 1642 may include a lock that can reversibly hold the button 1696 in the desired position such as, for example, the locked position.

Figure 17:
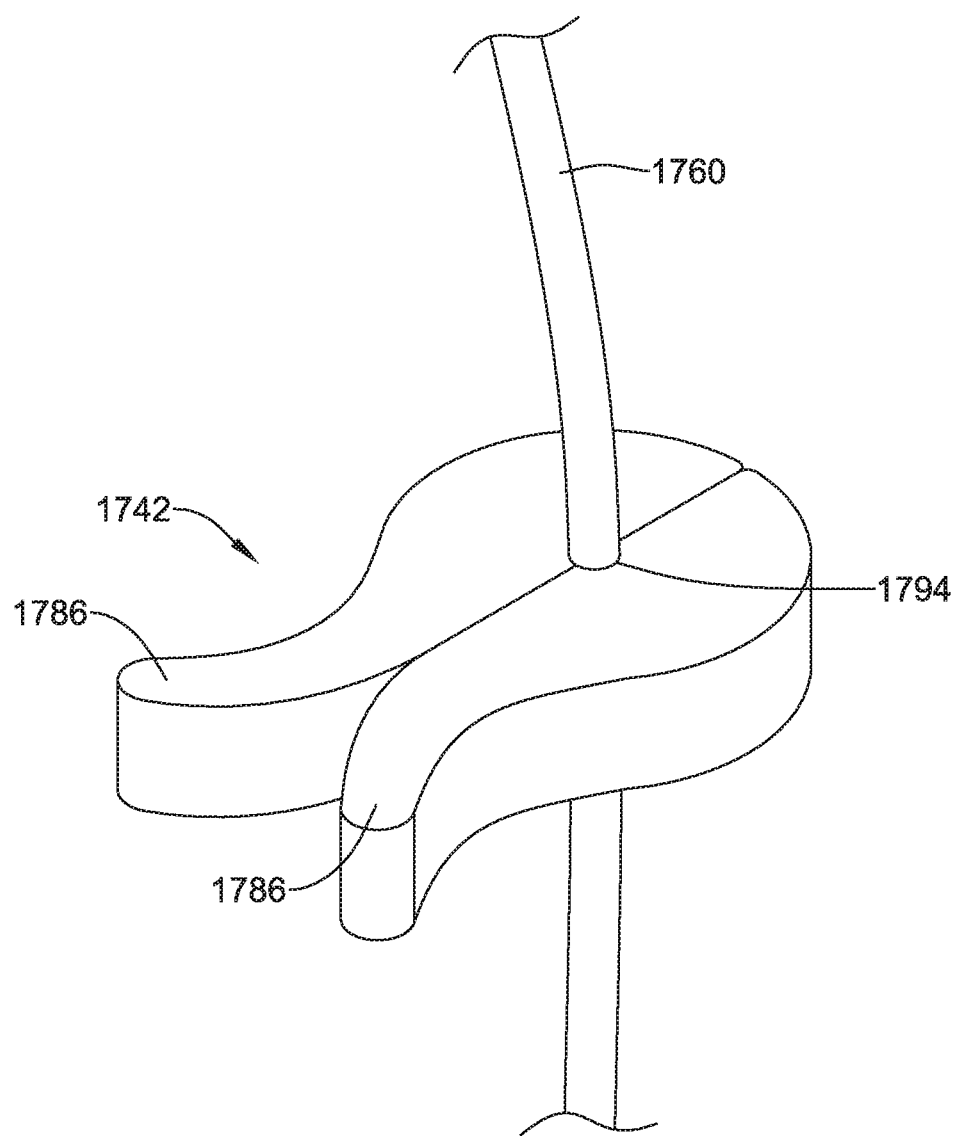
FIG. 17 is a perspective view of another example locking member.

FIG. 17 illustrates another example locking member 1742, which may be used with any of the biopsy caps disclosed herein. The locking member 1742 may include a pair of arms 1786 that can be actuated to open/close opening 1794 to secure the device 1760. The locking member 1742 may function in a manner similar to a clothespin. As such, the locking member 1742 may include a spring or other biasing member (not shown) that holds it in either the open (e.g., "unlocked") or closed (e.g., "locked") positions.

Figure 18:
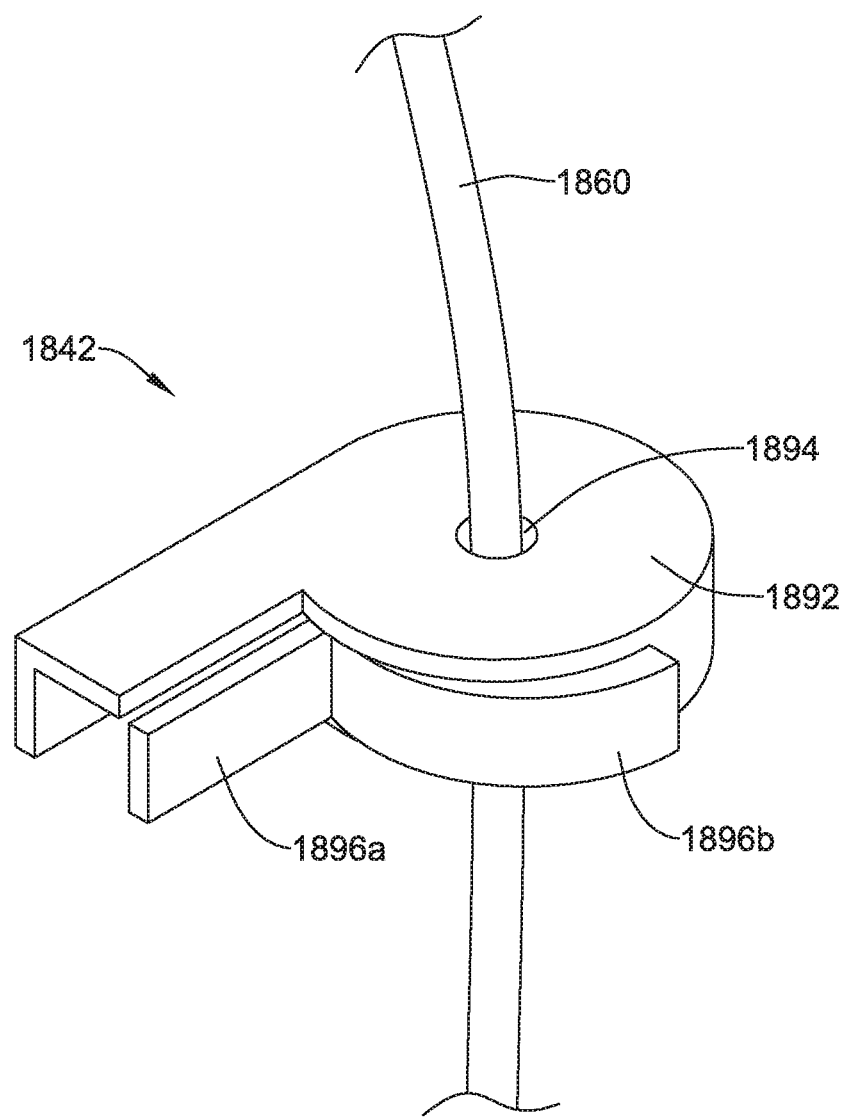
FIG. 18 is a perspective view of another example locking member.

FIG. 18 illustrates another example locking member 1842, which may be used with any of the biopsy caps disclosed herein. The locking member 1842 may include a base 1892 having opening 1894 formed therein. A device 1860 may extend therethrough. A pair of buttons 1896a/1896b may be attached to the base 1892 for opening/closing the opening 1894. For example, one of the buttons (e.g., button 1896b) may be depressed to "lock" the device 1860 while the other button (e.g., button 1896a) may be depressed to open or "unlock" the device 1860.

Figure 19A:
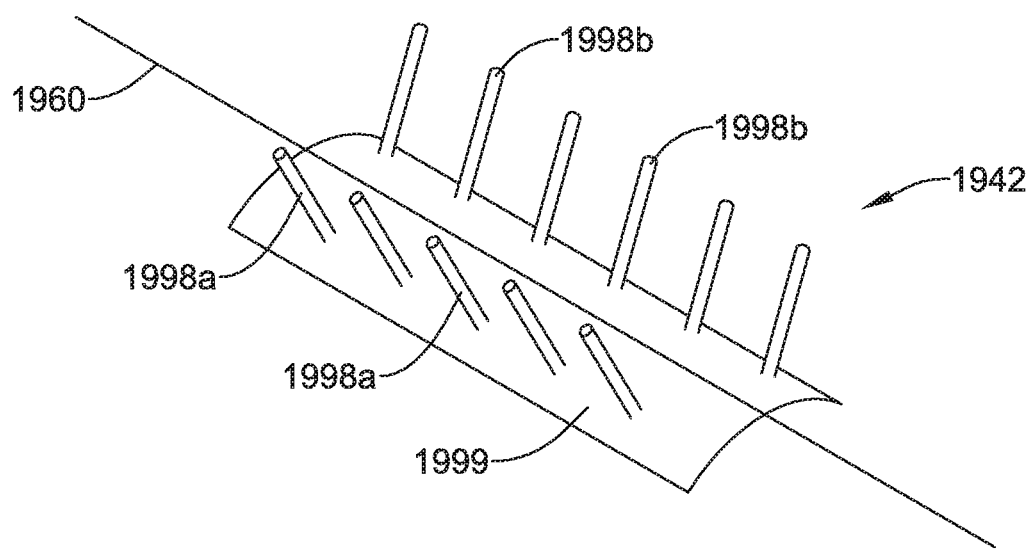
FIG. 19A is a perspective view of another example locking member in a first configuration.
Figure 19B:
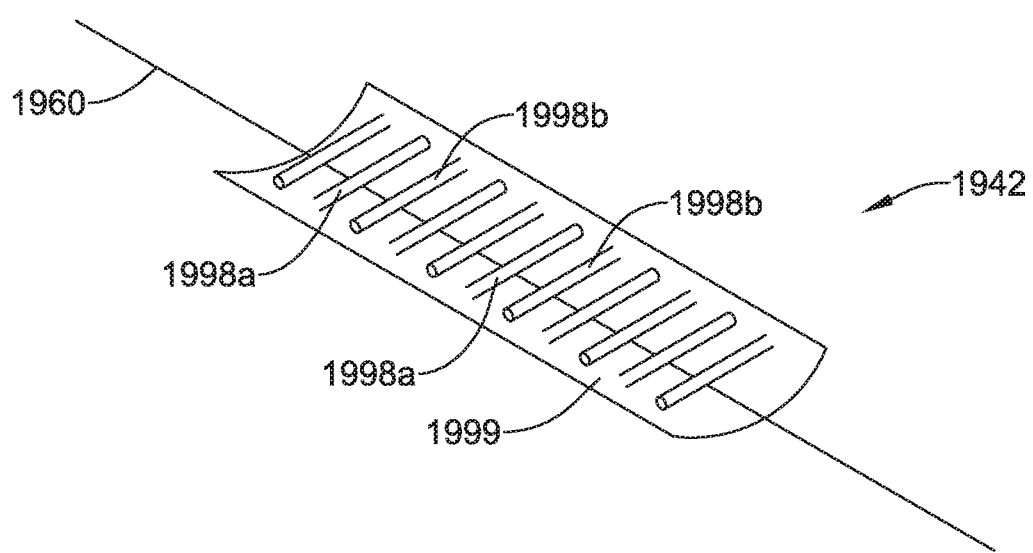
FIG. 19B is a perspective view of the example locking member illustrated in FIG. 19A in a second configuration.
Figure 20A:
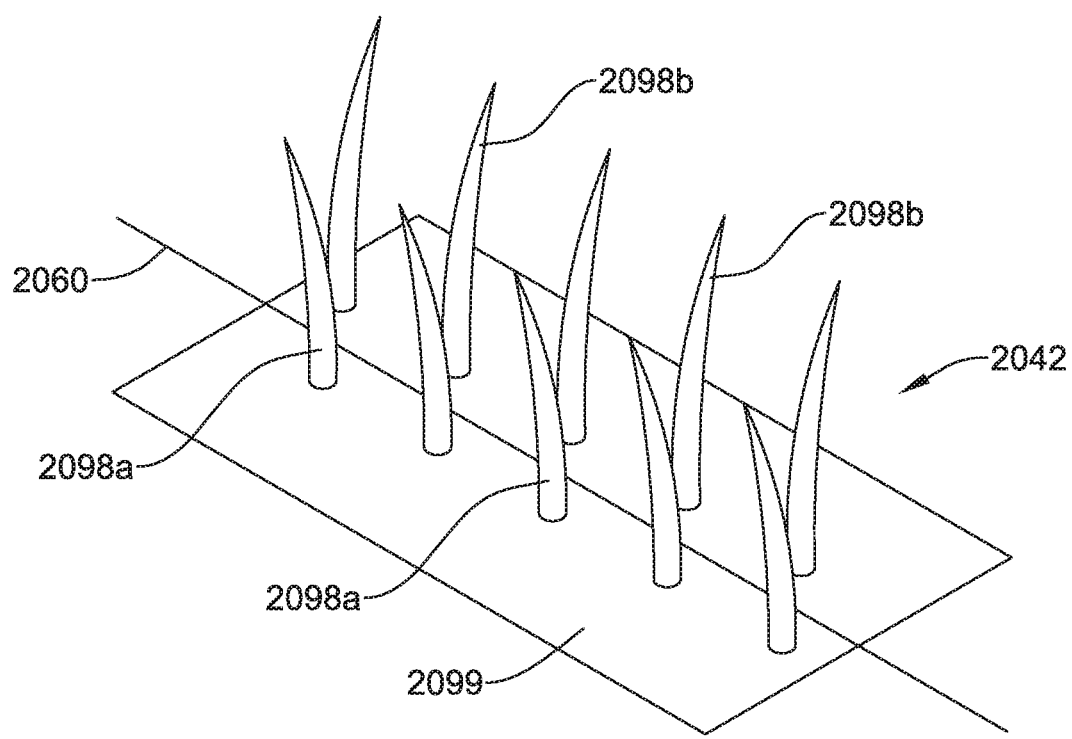
FIG. 20A is a perspective view of another example locking member in a first configuration.
Figure 20B:
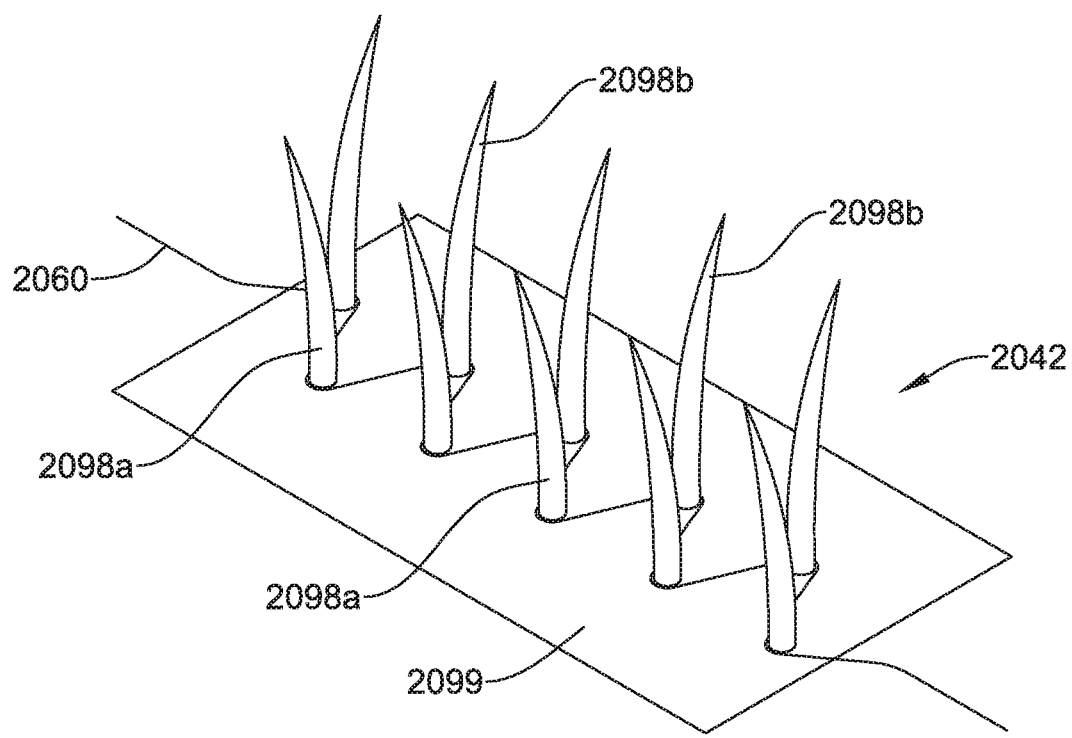
FIG. 20B is a perspective view of the example locking member illustrated in FIG. 20A in a second configuration.

FIGS. 19A and 19B illustrate locking member 1942, which may be configured to shift between a first or open configuration (as illustrated in FIG. 19A) and a second or closed configuration (as illustrated in FIG. 19B). The locking member 1942 may include a pair of opposing sets of fingers 1998a/1998b coupled to a base 1999 that are configured to shift from the upright or open first position to the horizontal or flat second configuration, the later being configured to secure the position of the device 1960. FIGS. 20A and 20B illustrate locking member 2042, which may be similar in form and function to the locking member 1942. The locking member 2042 may include a pair of opposing sets of fingers 2098a/2098b coupled to a base 2099. A device 2060 may extend through the fingers 2098a/2098b as shown in FIG. 20A, which may hold device 2060 in place, for example, by friction. Alternatively, the device 2060 may be wrapped around fingers 2098a/2098b, as shown in FIG. 20B.

In some embodiments, the bases 1999 and/or 2099 may be generally planar. In other embodiments, the bases 1999 and/or 2099 may be curved so as to be convex, concave, or have another shape. Moreover, the bases 1999 and/or 2099 may change from one shape to another upon actuation of the fingers 1998a/1999b and/or 2098a/2098b. For example, the bases 1999 and/or 2099 may be generally planar when the fingers 1998a/1999b and/or 2098a/2098b are in the open position and the bases 1999 and/or 2099 may shift to a concave shape when the fingers 1998a/1999b and/or 2098a/2098b shift to the flat configuration. Alternatively, the bases 1999 and/or 2099 may shift from concave to planar, convex to planar, planar to convex, etc.

A number of alternatives are also contemplated for the fingers 1998a/1999b and/or 2098a/2098b. For example, the fingers 1998a/1999b and/or 2098a/2098b may be interconnected so that the shifting of one finger results in the shifting of all the fingers. Alternatively, flaps may be used instead of or in addition to the fingers 1998a/1999b and/or 2098a/2098b that extend down at least a portion of the length of the bases 1999 and/or 2099 and that are configured to shift between an open and a closed configuration.

The base 1999/2099 of locking members 1942/2042 may desirably add a surface substrate that may allow these devices to be attached to a biopsy cap. In some embodiments, the base 1999/2099 may include a strip of polymer or plastic that can be bonded to a biopsy cap with a permanent adhesive. In other embodiments, the base 1999/2099 may be configured to be removably attached to the biopsy cap. For example, a removable or temporary adhesive may be used, the base 1999/2099 may be "velcroed" onto the cap, etc.

Figure 21A:
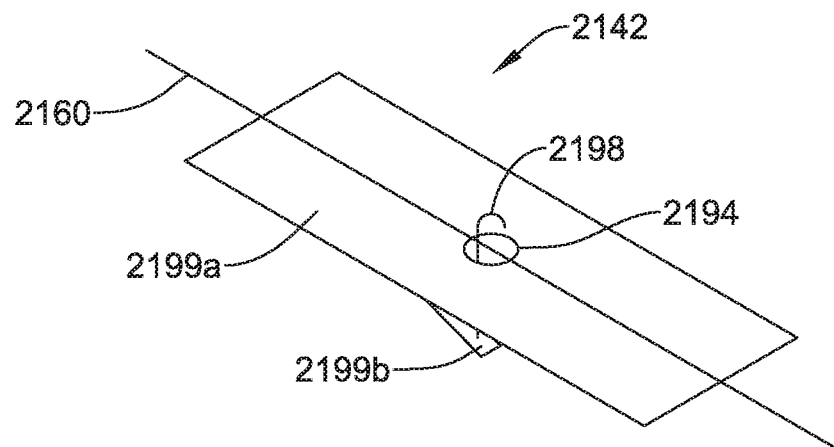
FIG. 21A is a perspective view of another example locking member in a first configuration.
Figure 21B:
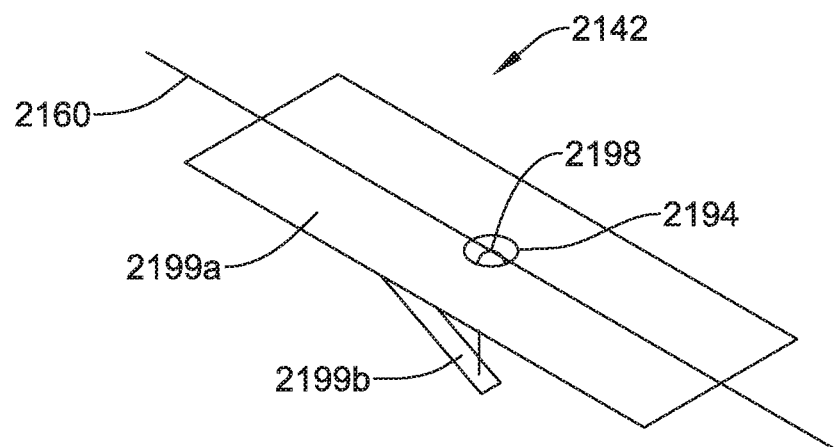
FIG. 21B is a perspective view of the example locking member illustrated in FIG. 21A in a second configuration.

FIGS. 21A and 21B illustrate locking member 2142, which may be configured to shift between a first configuration (as illustrated in FIG. 21A) and a second configuration (as illustrated in FIG. 21B). The locking member 2142 may include a base 2199a including a platform region 2199b. The region 2199b may include a hook-like extension 2198 that extends through an opening 2194 in the base 2199a and that can grasp a device 2160 when actuated (as illustrated in FIG. 21A). The region 2199b may be hingedly connected to the base 2199a so that the region 2199b can be moved up or down, as desired, to engage the device 2160. In alternative embodiments, multiple hook-like extensions 2198 may be utilized. Furthermore, hook-like extensions 2198 having different shapes may also be utilized such as longer hooks, wider hooks, two or more opposing hooks, eyelets, etc.

Figure 22:
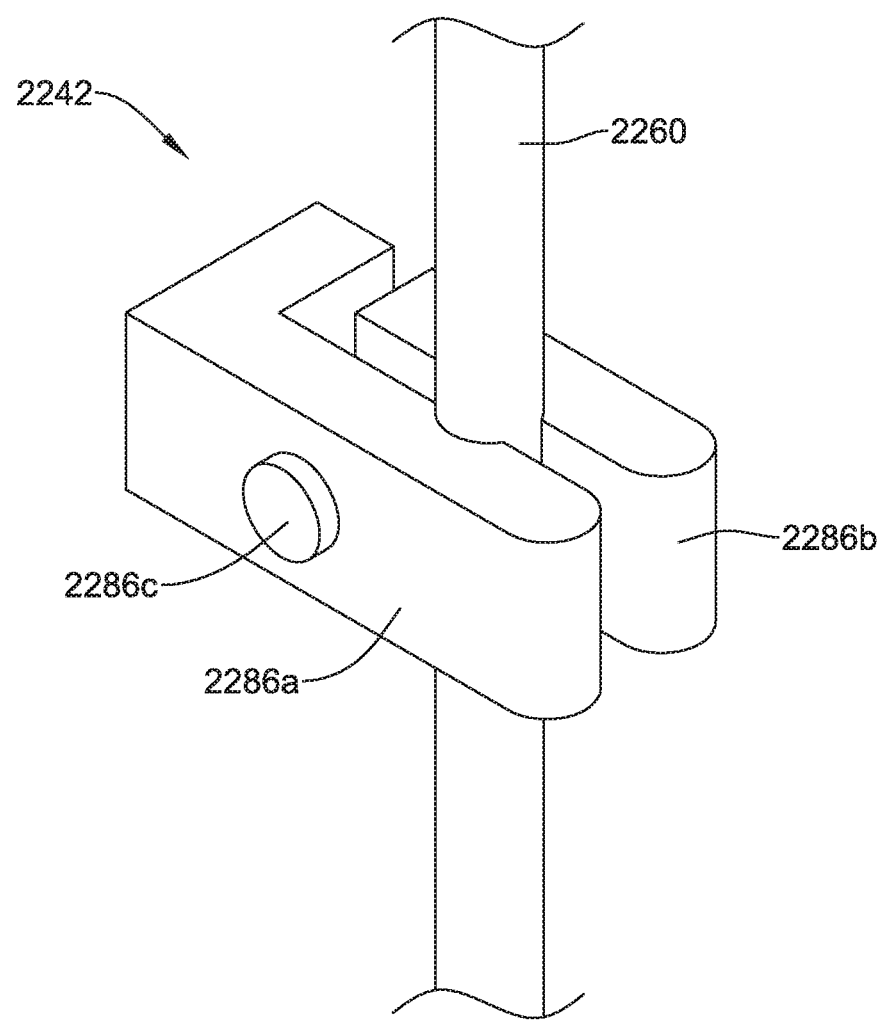
FIG. 22 is a perspective view of another example locking member.

FIG. 22 illustrates another example locking device 2260, which may be used with any of the biopsy caps disclosed herein. The device 2260 may include a pair of arm segments 2286a/2286b coupled together by a linkage 2286c. The linkage 2286c may be slidable within one of the arm segments 2286a/2286b so that the arms 2286a/2286b can be brought into closer contact with one another by pinching together the arms 2286a/2286b and locking the position of the device 2260. Manually moving the arms 2286a/2286b further apart may release the device 2260.

In some embodiments, one or more additional locking members may be added to a cap. The additional locking member may take any suitable form including any of those disclosed herein. Adding the locking members may include fastening, snapping on, or hingedly connecting an external locking member assembly onto the cap. Some additional discussion of wire or other locking devices which may be suitable for use with a biopsy cap may include U.S. Patent Application Pub Nos. US20060229496A1, US20050148820A1, and US20040106852A1as well as U.S. Pat. Nos. 7,060,052, 7,037,293, 6,893,393, 6,663,597, and 6,096,009, the entire disclosures of which are herein incorporated by reference.

The various caps as well as the various components thereof may be manufactured according to essentially any suitable manufacturing technique including molding, casting, mechanical working, and the like, or any other suitable technique. Furthermore, the various structures may include materials commonly associated with medical devices such as metals, metal alloys, polymers, metal-polymer composites, ceramics, combinations thereof, and the like, or any other suitable material. These materials may include transparent or translucent materials to aid in visualization during the procedure. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; combinations thereof; and the like; or any other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane, polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like.

In at least some embodiments, portions or all of the structures disclosed herein may also be doped with, made of, or otherwise include a radiopaque material. Radiopaque materials are understood to be materials capable of producing a relatively bright image on a fluoroscopy screen or another imaging technique during a medical procedure. This relatively bright image aids the user of endoscope 10 in determining its location. Some examples of radiopaque materials can include, but are not limited to, gold, platinum, palladium, tantalum, tungsten alloy, polymer material loaded with a radiopaque filler, and the like. Additionally, radiopaque marker bands and/or coils may be incorporated into the design of endoscope 10 or the various components thereof to achieve the same result.

In some embodiments, a degree of MRI compatibility may be imparted into the structures disclosed herein. For example, to enhance compatibility with Magnetic Resonance Imaging (MRI) machines, it may be desirable to make a portion of the endoscope 10 in a manner that would impart a degree of MRI compatibility. For example, a portion of the endoscope 10 may be made of a material that does not substantially distort the image and create substantial artifacts (artifacts are gaps in the image). Certain ferromagnetic materials, for example, may not be suitable because they may create artifacts in an MRI image. A portion of the endoscope 10 may also be made from a material that the MM machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In addition, portions or components of the structures (including the various securing members, locking members, etc.) disclosed herein may be coated with a relatively soft material that may improve grip such as a thermoplastic elastomer. The coating may or may not include additional features that may improve grip such as ridges, surface textures, bumps, grooves, projections, etc.

Furthermore, the various structures disclosed herein may be designed for single use or may be designed for repeated uses. Thus, the structures disclosed herein may be manufactured from materials that can withstand multiple sterilizations and/or cleanings. This may be true of entire caps, as disclosed herein, or any of the various features of any of the caps.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A biopsy cap for use with a port of a medical device, the biopsy cap comprising:
    a base having a securing member for securing the biopsy cap to a port on the medical device;
    an outer shell securable to the base and defining an interior volume;
    a disk shutter section disposed within the interior volume and including a plurality of fins arranged in a helical fashion; and
    a brush section disposed within the interior volume adjacent the disk shutter section, the brush section including a plurality of brushes arranged in a helical fashion.

2. The biopsy cap of claim 1, further comprising a locking member coupled to the outer shell.

3. The biopsy cap of claim 1, wherein the disk shutter section includes a central aperture extending axially therethrough and the plurality of fins are adapted to bend away from the central aperture in response to an elongate member being passed through the disk shutter section but the plurality of fins are biased towards the elongate member.

4. The biopsy cap of claim 3, wherein the elongate member comprises a C-shaped channel, and at least some of the plurality of fins are adapted to extend into the C-shaped channel to at least partially block fluid flow through the biopsy cap along the C-shaped channel.

5. The biopsy cap of claim 1, wherein the brush section includes a central aperture extending axially therethrough and the plurality of brushes are adapted to bend away from the central aperture in response to an elongate member being passed through the brush section but the plurality of brushes are biased towards the elongate member.

6. The biopsy cap of claim 5, wherein the elongate member comprises a C-shaped channel, and at least some of the plurality of brushes are adapted to extend into the C-shaped channel to at least partially block fluid flow through the biopsy cap along the C-shaped channel.

7. The biopsy cap of claim 1, wherein the brush section comprises a plurality of individual brush layers stacked together, where each individual brush layer comprises:
    an outer annular ring; and
    several of the plurality of brushes, each secured to the outer annular ring and extending towards a center point of the individual brush layer, each radially spaced apart along the outer annular ring;
    wherein each individual brush layer is rotated relative to adjacent individual brush layers such that the plurality of brushes are arranged in a helix.

8. The biopsy cap of claim 1, wherein the brush section comprises a plurality of brush section portions that are individually molded and then adhered together to form the brush section.

9. The biopsy cap of claim 1, wherein the brush section is molded as a linear shape having a first end and a second end, and the first end and the second end are subsequently joined together to form the brush section.

10. The biopsy cap of claim 1, wherein the brush section comprises a plurality of brush layers that are secured to each other and sequentially folded together to form the brush section.

11. The biopsy cap of claim 1, further comprising a hydrophilic foam section disposed within the interior volume adjacent the brush section.

12. A biopsy cap configured to be secured to a port of a medical device, the biopsy cap comprising:
    an outer shell securable to a port on the medical device and defining an interior volume;
    a brush section disposed within the interior volume, and including a plurality of brushes;
    a disk shutter section disposed within the interior volume and including a plurality of fins; and
    a hydrophilic foam section disposed within the interior volume adjacent the brush section.

13. The biopsy cap of claim 12, wherein the plurality of brushes and the plurality of fins are each arranged in a helical fashion, and the disk shutter section is disposed adjacent the brush section.

14. The biopsy cap of claim 12, wherein the brush section includes a central aperture extending axially therethrough and the plurality of brushes are adapted to bend away from the central aperture in response to an elongate member being passed through the brush section but the plurality of brushes are biased towards the elongate member.

15. The biopsy cap of claim 14, wherein the elongate member comprises a C-shaped channel, and at least some of the plurality of brushes are adapted to extend into the C-shaped channel to at least partially block fluid flow through the biopsy cap along the C-shaped channel.

16. The biopsy cap of claim 12, wherein the brush section comprises a plurality of individual brush layers stacked together, where each individual brush layer comprises:
    an outer annular ring; and
    several of the plurality of brushes, each secured to the outer annular ring and extending towards a center point of the individual brush layer, each radially spaced apart along the outer annular ring;
    wherein each individual brush layer is rotated relative to adjacent individual brush layers such that the plurality of brushes are arranged in a helix.

17. The biopsy cap of claim 12, wherein the brush section comprises a plurality of brush section portions that are individually molded and then adhered together to form the brush section.

18. The biopsy cap of claim 12, wherein the brush section is molded as a linear shape having a first end and a second end, and the first end and the second end are subsequently joined together to form the brush section.

19. The biopsy cap of claim 12, wherein the brush section comprises a plurality of brush layers that are secured to each other and sequentially folded together to form the brush section.

20. A biopsy cap for use with a port on a medical device, the biopsy cap comprising:
    a base having a securing member for securing the biopsy cap to a port on the medical device, the base including an aperture to accommodate an elongate member extendable through the biopsy cap;
    an outer shell securable to the base and defining an interior volume, the outer shell including an aperture to accommodate the elongate member extendable through the biopsy cap;
    a disk shutter section disposed within the interior volume and including a plurality of fins arranged in a helical fashion, the plurality of fins extending towards an aperture to accommodate the elongate member; and
    a brush section disposed within the interior volume adjacent the disk shutter section, the brush section including a plurality of brushes arranged in a helical fashion, the plurality of brushes extending towards an aperture to accommodate the elongate member.

* * * * *